United States Patent
Ilag et al.

(10) Patent No.: US 10,226,502 B2
(45) Date of Patent: Mar. 12, 2019

(54) SUGAR EXTRACT

(71) Applicant: THE PRODUCT MAKERS (AUSTRALIA) PTY LTD, Keysborough (AU)

(72) Inventors: Leodevico Luna Ilag, Balwyn (AU); Jason Smythe, Mentone (AU); Timothy Peter Ellis, Glen Waverley (AU); Richard Stuart Weisinger, Ringwood North (AU)

(73) Assignee: THE PRODUCT MAKERS (AUSTRALIA) PTY LTD, Keysborough (AU)

( * ) Notice: Subject to any disclaimer, the term of this patent is extended or adjusted under 35 U.S.C. 154(b) by 0 days.

(21) Appl. No.: 15/625,427

(22) Filed: Jun. 16, 2017

(65) Prior Publication Data

US 2017/0281706 A1    Oct. 5, 2017

Related U.S. Application Data

(62) Division of application No. 15/380,388, filed on Dec. 15, 2016, which is a division of application No. 13/984,328, filed as application No. PCT/AU2012/000115 on Feb. 8, 2012, now Pat. No. 9,572,852.

(30) Foreign Application Priority Data

Feb. 8, 2011 (AU) ............... 2011900400
Jun. 21, 2011 (AU) ............... 2011902446

(51) Int. Cl.
*A61K 36/00* (2006.01)
*A61K 36/899* (2006.01)

(52) U.S. Cl.
CPC ................. *A61K 36/899* (2013.01)

(58) Field of Classification Search
None
See application file for complete search history.

(56) References Cited

U.S. PATENT DOCUMENTS

| | | | |
|---|---|---|---|
| 1,730,473 A | 10/1929 | Olivarius |
| 2,000,202 A | 5/1935 | Vasquez |
| 2,170,713 A | 8/1939 | Fattinger |
| 2,342,162 A | 2/1944 | Musher |
| 3,174,877 A | 3/1965 | Bohrer |
| 3,325,308 A | 6/1967 | Othmer |
| 3,619,293 A | 11/1971 | Niimi et al. |
| 3,975,205 A | 8/1976 | Munir et al. |
| 4,101,338 A | 7/1978 | Rapaport et al. |
| 4,102,646 A | 7/1978 | Sleeter |
| 4,111,714 A | 9/1978 | Hippchen et al. |
| 4,116,712 A | 9/1978 | Othmer |
| 4,333,770 A | 6/1982 | Neuzil et al. |
| 4,359,430 A | 11/1982 | Heikkila et al. |
| 4,404,037 A | 9/1983 | Broughton |
| 4,523,959 A | 6/1985 | Exertier |
| 4,523,999 A | 6/1985 | Toyoshi et al. |
| 5,002,614 A | 3/1991 | Miyagi et al. |
| 5,096,594 A | 3/1992 | Rabinowitz |
| 5,127,957 A | 7/1992 | Heikkila et al. |
| 5,252,136 A | 10/1993 | Desforges et al. |
| 5,382,294 A | 1/1995 | Rimedio et al. |
| 5,384,035 A | 1/1995 | Smolnik et al. |
| 5,454,875 A | 10/1995 | Clarke |
| 5,482,631 A | 1/1996 | Saska et al. |
| 5,556,546 A | 9/1996 | Tanimura et al. |
| 5,578,336 A | 11/1996 | Monte |
| 5,663,156 A | 9/1997 | Granja et al. |
| 5,955,269 A | 9/1999 | Ghai et al. |
| 6,093,326 A | 7/2000 | Heikkila et al. |
| 6,099,654 A | 8/2000 | Kaneko et al. |
| 6,217,664 B1 | 4/2001 | Baniel |
| 6,372,049 B1 | 4/2002 | Shimanskaya et al. |
| 6,406,547 B1 | 6/2002 | Donovan et al. |
| 6,406,548 B1 | 6/2002 | Donovan et al. |
| 6,475,390 B1 | 11/2002 | Durham et al. |
| 6,528,099 B1 | 3/2003 | Garti et al. |
| 6,630,672 B1 | 10/2003 | Brotherton et al. |
| 6,723,369 B2 | 4/2004 | Burgess |
| 6,777,397 B2 | 8/2004 | Zehner et al. |

(Continued)

FOREIGN PATENT DOCUMENTS

AU        668305 B2      4/1996
AU      2011204847 A1    8/2011

(Continued)

OTHER PUBLICATIONS

Vercellotti et al. (1998) "Chemistry of Membrane Separation Processes in Sugar Industry Applications. Part I. Composition of Membrane Fouling Materials; Part II Treatment to Remove Membrane Fouling Materials," Sugar Industry Technologists Annual Meeting. S.I.T. Paper No. 727. 30 pgs.

Vercellotti et al. (1998) "Membrane Separation Chemistry in Sugar Processing Applications," Proceedings of the Conference on Sugar Processing Research. 35 pgs.

Vermunt et al. (2003) "Effects of sugar intake on body weight: a review," The International Association for the Study of Obesity. Obesity Reviews. 4:91-99.

(Continued)

*Primary Examiner* — Qiuwen Mi
(74) *Attorney, Agent, or Firm* — Brian C. Trinque; Lathrop Gage LLP

(57) ABSTRACT

This invention relates to novel extracts from sugar cane and sugar beet molasses and the characterization of those extracts. The extracts are enriched in hydrophobic compounds including polyphenols, in levels 5 to 10 fold higher than found in molasses itself methods for extracting the extract are also described, together with new uses for the extracts as food ingredients, food modifiers and therapeutic substances.

20 Claims, 12 Drawing Sheets

Specification includes a Sequence Listing.

(56) References Cited

U.S. PATENT DOCUMENTS

| | | |
|---|---|---|
| 6,869,625 B2 | 3/2005 | Gupta et al. |
| 6,885,003 B1 | 4/2005 | Dubernet |
| 7,015,339 B2 | 3/2006 | Khare et al. |
| 7,122,574 B2 | 10/2006 | Romanczyk, Jr. et al. |
| 7,150,885 B2 | 12/2006 | Araki et al. |
| 7,312,199 B2 | 12/2007 | Burdick et al. |
| 8,138,162 B2 | 3/2012 | Kannar et al. |
| 9,364,016 B2 | 6/2016 | Kannar et al. |
| 9,572,852 B2 | 2/2017 | Ilag et al. |
| 9,717,771 B2 | 8/2017 | Ilag et al. |
| 2001/0001178 A1 | 5/2001 | Donovan et al. |
| 2001/0001956 A1 | 5/2001 | Hyoky et al. |
| 2002/0150652 A1 | 10/2002 | Antila et al. |
| 2002/0169311 A1 | 11/2002 | Paananen et al. |
| 2002/0187219 A1 | 12/2002 | Yang et al. |
| 2002/0197380 A1 | 12/2002 | Mantius et al. |
| 2003/0082287 A1 | 5/2003 | Wolt et al. |
| 2003/0124170 A1 | 7/2003 | Gallaher et al. |
| 2003/0124208 A1 | 7/2003 | Makino et al. |
| 2003/0147978 A1 | 8/2003 | Araki et al. |
| 2003/0161903 A1 | 8/2003 | Konishi et al. |
| 2003/0165574 A1 | 9/2003 | Ward et al. |
| 2003/0198694 A1 | 10/2003 | Chou |
| 2003/0232763 A1 | 12/2003 | Jia |
| 2004/0001862 A1 | 1/2004 | Xiu |
| 2004/0006222 A1 | 1/2004 | Paananen et al. |
| 2004/0006223 A1 | 1/2004 | Karki et al. |
| 2004/0052915 A1 | 3/2004 | Carlson et al. |
| 2004/0060868 A1 | 4/2004 | Heikkila et al. |
| 2004/0081734 A1 | 4/2004 | Lang |
| 2004/0097429 A1 | 5/2004 | Nieuwenhuizen et al. |
| 2004/0131749 A1 | 7/2004 | Gabriel et al. |
| 2004/0151815 A1 | 8/2004 | Jensen et al. |
| 2004/0191336 A1 | 9/2004 | Hilaly et al. |
| 2004/0197380 A1 | 10/2004 | Wolf et al. |
| 2005/0175674 A1 | 8/2005 | Lang et al. |
| 2005/0181074 A1 | 8/2005 | Watson et al. |
| 2005/0214419 A1 | 9/2005 | Aberle et al. |
| 2006/0003029 A1 | 1/2006 | Nash et al. |
| 2006/0121158 A1 | 6/2006 | Ferruzzi et al. |
| 2006/0147556 A1 | 7/2006 | Brewer |
| 2007/0014912 A1 | 1/2007 | Mazza et al. |
| 2007/0158269 A1 | 7/2007 | Paananen et al. |
| 2007/0160698 A1 | 7/2007 | Waga et al. |
| 2007/0166246 A1 | 7/2007 | Takagaki et al. |
| 2007/0178175 A1 | 8/2007 | Matsubara et al. |
| 2007/0190209 A1 | 8/2007 | Sinnott |
| 2008/0286254 A1 | 11/2008 | Sakamoto et al. |
| 2009/0047368 A1 | 2/2009 | Numata et al. |
| 2009/0053333 A1 | 2/2009 | Sambanthamurthi et al. |
| 2009/0281057 A1 | 11/2009 | Bhaskaran et al. |
| 2010/0112099 A1 | 5/2010 | Tripp et al. |
| 2010/0130422 A1 | 5/2010 | Bernaert et al. |
| 2010/0166851 A1 | 7/2010 | Dallas |
| 2010/0184666 A1 | 7/2010 | Bernaert et al. |
| 2010/0196549 A1 | 8/2010 | Rivera et al. |
| 2012/0115941 A1 | 5/2012 | Payn et al. |
| 2014/0315993 A1 | 10/2014 | Kannar et al. |
| 2015/0201660 A1 | 7/2015 | Kannar et al. |
| 2016/0193275 A1 | 7/2016 | Ilag et al. |
| 2016/0263177 A1 | 9/2016 | Kannar et al. |

FOREIGN PATENT DOCUMENTS

| | | |
|---|---|---|
| BR | PI0303976 A | 6/2005 |
| CA | 2053412 A1 | 4/1992 |
| CA | 2420881 A1 | 3/2002 |
| CN | 1484974 A | 3/2004 |
| CN | 1685929 A | 10/2005 |
| CN | 101317850 A | 12/2008 |
| CN | 101835390 A | 9/2010 |
| DE | 3232693 A1 | 7/1983 |
| EP | 1 362 517 A1 | 11/2003 |
| EP | 1 362 919 A1 | 11/2003 |
| EP | 1 447 013 A1 | 8/2004 |
| EP | 1 447 014 A1 | 8/2004 |
| EP | 2 022 344 A1 | 2/2009 |
| EP | 1 466 609 B2 | 9/2009 |
| EP | 2 250 911 A1 | 11/2010 |
| FR | 2797688 A1 | 2/2001 |
| FR | 2929852 A1 | 10/2009 |
| IN | 230486 A | 3/2009 |
| JP | S53-059044 A | 5/1978 |
| JP | S58-144382 A | 8/1983 |
| JP | S59-020223 A | 2/1984 |
| JP | S61-069727 A | 4/1986 |
| JP | S61-083130 A | 4/1986 |
| JP | S61-139400 A | 6/1986 |
| JP | S61-265068 A | 11/1986 |
| JP | S61-268200 A | 11/1986 |
| JP | S62-126951 A | 6/1987 |
| JP | S63-207400 A | 8/1988 |
| JP | H01-244000 A | 9/1989 |
| JP | H02-020300 A | 1/1990 |
| JP | H03-145424 | 6/1991 |
| JP | H04-320691 A | 11/1992 |
| JP | H05-211900 A | 8/1993 |
| JP | H06-062798 A | 3/1994 |
| JP | H08-040912 A | 2/1996 |
| JP | H09-025290 A | 1/1997 |
| JP | H11-075758 A | 3/1999 |
| JP | H11-318405 A | 11/1999 |
| JP | 2000-032954 A | 2/2000 |
| JP | 2000-297045 A | 10/2000 |
| JP | 2001-112439 A | 4/2001 |
| JP | 2001-131080 A | 5/2001 |
| JP | 2001-200250 A | 7/2001 |
| JP | 2001-302533 A | 10/2001 |
| JP | 2002-020306 A | 1/2002 |
| JP | 2002-161046 A | 6/2002 |
| JP | 2003-063975 A | 3/2003 |
| JP | 2003-116486 A | 4/2003 |
| JP | 2003-137803 A | 5/2003 |
| JP | 2004-065018 A | 3/2004 |
| JP | 2004-075612 A | 3/2004 |
| JP | 2004-331512 A | 11/2004 |
| JP | 2005-278407 A | 10/2005 |
| JP | 2005-343843 A | 12/2005 |
| JP | 2006-028020 A | 2/2006 |
| JP | 2006-131578 A | 5/2006 |
| JP | 2006-321772 A | 11/2006 |
| JP | 2007-043940 A | 2/2007 |
| JP | 2007-063221 A | 3/2007 |
| JP | 2008-044872 A | 2/2008 |
| JP | 2008-222656 A | 9/2008 |
| JP | 2009-298769 A | 12/2009 |
| KR | 100894911 B1 | 4/2009 |
| KR | 10-2009-0063794 A | 6/2009 |
| RU | 2048847 A | 5/1997 |
| WO | 1989/001295 A1 | 2/1989 |
| WO | 1994/012057 A1 | 6/1994 |
| WO | 1997/049734 A1 | 12/1997 |
| WO | 1998/029571 A1 | 7/1998 |
| WO | 1998/055658 A2 | 12/1998 |
| WO | 2001/036690 A1 | 5/2001 |
| WO | 2001/078629 A1 | 10/2001 |
| WO | 2001/098544 A2 | 12/2001 |
| WO | 2002/014477 A2 | 2/2002 |
| WO | 2002/020112 A1 | 3/2002 |
| WO | 2002/078469 A1 | 10/2002 |
| WO | 2003/074144 A2 | 9/2003 |
| WO | 2003/074145 A1 | 9/2003 |
| WO | 2003/075685 A2 | 9/2003 |
| WO | 2003/099309 A1 | 12/2003 |
| WO | 2004/014159 A1 | 2/2004 |
| WO | 2005/006891 A1 | 1/2005 |
| WO | 2005/052195 A1 | 6/2005 |
| WO | 2005/084457 A1 | 9/2005 |
| WO | 2005/089066 A2 | 9/2005 |
| WO | 2005/105852 A1 | 11/2005 |
| WO | 2005/117608 A1 | 12/2005 |
| WO | 2006/014028 A1 | 2/2006 |
| WO | 2006/052007 A1 | 5/2006 |
| WO | 2006/128253 A1 | 12/2006 |

(56) References Cited

FOREIGN PATENT DOCUMENTS

| | | |
|---|---|---|
| WO | 2006/128259 A1 | 12/2006 |
| WO | 2007/041817 A1 | 4/2007 |
| WO | 2008/034180 A1 | 3/2008 |
| WO | 2008/142178 A1 | 11/2008 |
| WO | 2009/015996 A2 | 2/2009 |
| WO | 2009/043100 A1 | 4/2009 |
| WO | 2009/046492 A1 | 4/2009 |
| WO | 2009/049428 A1 | 4/2009 |
| WO | 2009/136219 A1 | 11/2009 |
| WO | 2010/039019 A1 | 4/2010 |
| WO | 2010/094837 A2 | 8/2010 |
| WO | 2010/094860 A1 | 8/2010 |
| WO | 2010/118474 A1 | 10/2010 |
| WO | 2012/106761 A1 | 8/2012 |

OTHER PUBLICATIONS

Wachowicz (1978) "Possible use of gel filtration in the separation of substances of colored sugar solutions," Gazeta Cukrownicza. 86(6):125-7.—CASPLUS Abstract Only. CASPLUS Accession No. 1978:548469.

Wang et al. (2008) "A new green technology for direct production of low molecular weight chitosan," Carbohydrate Polymers. 74:127-132.

Weisinger et al. (2009) "Sugarcane-derived polyphenols decrease diet-induced obesity," Appetite 52:864.—Abstract Only.

Winter et al. (1992) "Experimental evidence for the effects of polyphenolic compounds from Dictyoneurum califomicum Ruprecht (Phaeophyta: Laminariales) on feeding rate and growth in the red abalone Haliotus rufescens Swainson," Journal of Experimental Marine Biology and Ecology. 155:263-277.

Wu et al. (2002) "Determination of molecular of pigment from molasses alcohol stillage," Huanjing Wuran Yu Fangzhi. 24(1):13-15.—Abstract Only.

Wu et al. (2005) "Tea and circulating estrogen levels in postmenopausal Chinese women in Singapore," Carcinogenesis. 26(5):976-980.

Xian et al. (2007) "Protective effects of tea polyphenols on cerebral nerve cell apoptosis induced by D-galactose and beta-amyloid peptide 25-35," Journal of Clinical Rehabilitative Tissue Engineering Research. 11(43):8805-8808.

Yinfa et al. (2003) "Application of Food Glycemic Index in Diabetes Nutrition Education," Acta Nutrimenta Sinica. 25 (3):248-251.

Yoshikawa et al. (1996) "Medicinal Foodstuff. III. Sugar Beet. (1): Hypoglycemic Oleanolic Acid Oligoglycosides, Betavulgarosides I, II, III, and IV, From the Root of Beta *Vulgaris* L. (Chenopodiaceae)," Chem. Pharm. Bull. 44 (6):1212-1217.

Zemel (2002) "Regulation of Adiposity and Obesity Risk by Dietary Calcium: Mechanisms and Implications," J. Am. College Nutr. 21(2):146S-151S.

Zhang et al. (2007) "Antidiabetic properties of polysaccharide- and polyphenolic-enriched fractions from the brown seaweed Ascophyllum nodosum," Can. J. Physiol. Pharmacol. 85:1116-1123.

Zhang et al. (2009) "Protective role of tea polyphenols in oxidative stress damage of rat articular cartilage issue caused by brick-tea fluorosis," Zhongquo Difangbingxue Zazhi. 28(4):381-385.—Abstract Only.

Zheng et al. (2004) "Anti-Obesity Effects of Three Major Components of Green Tea, Catechins, Caffeine and Theanine, in Mice," In Vivo. 18:55-62.

Zielinska-Przyjemska et al. (2005) "Effect of tea polyphenols on the oxidative metabolism of polymorphonuclear neutrophils in healthy and obese people," Polski Merkuriusz Lekarski. 19(109):41-47.—Abstract Only.

Zielinska-Przyjemska et al. (2007) "Effects of Aronia Melanocarpa Polyphenols on Oxidative Metabolism and Apoptosis of Neutrophils from Obese and Non-Obese Individuals," Acta Sci. Pol. Technol. Aliment. 63:75-87.

Extended European Search Report corresponding to European Application No. 12744261.4, dated Oct. 28, 2014.

Supplementary Partial European Search Report corresponding to European Application No. 05744686.6, dated Jun. 26, 2009.

International Search Report with Written Opinion corresponding to International Patent Application No. PCT/AU2012/000115, dated Mar. 19, 2012.

Kajimoto et al. (2005) "Tea Catechins with a Galloyl Moiety Reduce Body Weight and Fat," J. Health Sci. 51 (2):161-171.

Kantachote et al. (2009) "Microbial succession in a fermenting of wild forest noni (Morinda coreia Ham) fruit plus molasses and its role in producing a liquid fertilizer," Electronic J. Biotech. 12(3):1-11.

Khan et al. (2010) "Exploiting phytochemicals for developing a 'push-pull' crop protection strategy for cereal farmers in Africa," J. Exp. Botany. 61(15):4185-4196.

Kim et al. (2003) "Antioxidant capacity of phenolic phytochemicals from various cultivars of plums," Food Chemistry. 81(3):321-326.—Abstract Only.

Kishihara et al. (1986) "Clarification of molasses through self-rejecting membrane formed dynamically on porous ceramic tube," Kagaku Kogaku Ronbunshu. 12(2):199-205.—Abstract Only.

Kita et al. (2004) "Intake of phytochemicals among Japanese, calculated by the new FFF database," BioFactors. 22:259-263.

Klasing et al. (1985) "Biological activity of phenolic compounds. Hepatic cytochrome P-450, cytochrome b5, and NADPH cytochrome c reductase in chicks and rats fed phenolic monomers, polymers, and glycosides," Proc. Soc. Exp. Biol. Med. 179:529-538.

Koge et al. (2005) "Antioxidants and Other Functional Extracts from Sugarcane," Ch. 15 In; Asian Functional Foods. pp. 411-431.

Kovacs et al. (2004) "Effects of green tea on weight maintenance after body-weight loss," British J. Nutr. 91:431-437.

Kumar et al. (1998) "Effect of Long Term Feeding of Urea Molasses Liquid Diet (UMLD) on Ovarian Activity in Crossbred Heifers," Indian Vet. Med. J. 22:185-188.

Lee et al. (2008) "Study on dietary habit and effect of onion powder supplementation on serum lipid levels in early diagnosed hyperlipidemic patients," Han'guk Sikp'um Yongyanq Kwahak Hoechi 37(5):561-570.—Abstract Only.

Livesey et al. (2008) "Fructose consumption and consequences for glycation, plasma triacylglycerol, and body weight: meta-analyses and meta-regression models of intervention studies," Am. J. Clin. Nutr. 88:1419-1437.

Lo Piparo et al. (2008) "Flavonoids for Controlling Starch Digestion: Structural Requirement for Inhibiting Human a-Amylase," J. Med. Chem. 51:3555-3561.

Loke et al. (2010) "Specific Dietary Polyphenols Attenuate Atherosclerosis in Apolipoprotein E-Knockout Mice by Alleviating Inflammation and Endothelial Dysfunction," Arterioscler. Thromb. Vasc. Biol. 30:749-757.

Machowetz et al. (2008) "Effect of Olive Oil Consumption on Serum Resistin Concentrations of Healthy Men," Horm. Metab. Res. 40:697-701.

Mantovani et al. (2004) "Cancer-Related Anorexia/Cachexia Syndrome and Oxidative Stress: An Innovative Approach beyond Current Treatment," Cancer Epidemiology, Biomarkers & Prevention. 13(10):1651-1659.

Mantovani et al. (2006) "A Phase II Study with Antioxidants, Both in the Diet and Supplemented, Pharmaconutritional Support, Progestagen, and Anti-Cyclooxygenase-2 Showing Efficacy and Safety in Patients with Cancer-Related Anorexia/Cachexia and Oxidative Stress," Cancer Epidemiology, Biomarkers & Prevention. 15 (5):1030-1034.

Mantovani et al. (2008) "Randomized phase III clinical trial of five different arms of treatment for patients with cancel cachexia: interim results," Nutrition. 24:305-313.

Mehra et al. (1998) "Effect of Restricted and Ad libitum Feeding of Urea Molasses Liquid Diet (UMLD) on the Performance of Adult Crossbred Cattle," Asian-Australas J. Anim. Sci. 11(1):30-34.

Melby et al. (2007) "Intake of phytochemicals by Japanese and its health effects," Daizu Tanpakushitsu Kenkyu. 9:138-146.—Abstract Only.

(56) References Cited

OTHER PUBLICATIONS

Nagao et al. (2009) "Visceral fat-reducing effect of continuous coffee beverage consumption in obese subjects," Japanese Pharmacology & Therapeutics. 37(4):333-344.—Abstract Only.

Nagasako-Akazome et al. (2007) "Apply Polyphenols Influence Cholesterol Metabolism in Healthy Subjects with Relatively High Body Mass Index," J. Oleo Sci. 56(8):417-428.

Nakamura et al. (2007) "Lowering effects on visceral fat of the OTPP (oolong tea polymerized polyphenols)-enriched polong tea (FOSHU "KURO-oolong tea OTPP") in over weight volunteers," Japanese Pharmacology & Therapeutics. 35(6):661-671.—Abstract Only.

Nakamura et al. (2008) "Lowering effects of the OTP (Oolong Tea Polymerized Polyphenols) enriched Oolong-Tea (FOSHU "KURO-Oolong Tea OTPP") on visceral fat in over weight volunteers," Japanese Pharmacology & Therapeutics. 36(4):347-357.—Abstract Only.

Ochiai et al. (2009) "Effects of hydroxyhydroquinone-reduced coffee on vasoreactivity and blood pressure," Hypertension Research. 32:969-974.

Olthof et al. (2000) "Metabolism of Chlorogenic Acid, Quercetin-3-rutinoside and Black Tea Polyphenols in Healthy Volunteers," Ch. 2.6 In; Spec. Publ. Royal Soc. Chem: 255 Dietary Anticarcinogens and Antimutagens. pp. 73-75.

Onimawo et al. (2010) "Assessment of Anemia and Iron Status of School Age Children (Aged 7-12 years) in Rural Communities of Abia State, Nigeria," African J. Food Agric. Nutr. Develop. 10(5):1-17.

Palfi et al. (2009) "Alcohol-free red wine inhibits isoproterenol-induced cardiac remodeling in rats by the regulation of Akt1 and protein kinase C alpha/beta II," J. Nutr. Biochem. 20:418-425.

Pasman et al. (2003) "Effect of two breakfasts, different in carbohydrate composition, on hunger and satiety and mood in healthy men," International Journal of Obesity. 27:663-668.

Patton et al. (2006) "Use of a spectrophotometric bioassay for determination of microbial sensitivity to manuka honey," J. Microbiological Methods. 64(1):84-95.—Abstract Only.

Payet et al. (2005) "Assessment of Antioxidant Activity of Cane Brown Sugars by ABTS and DPPH Radical Scavenging Assays: Determination of Their Polyphenolic and Volatile Constituents," J. Agric. Food Chem. 53:10074-10079.

Payet et al. (2006) "Comparison of the Concentrations of Phenolic Constituents in Cane Sugar Manufacturing Products with Their Antioxidant Activities," J. Agric. Food Chem. 54:7270-7276.

Pena et al. (2003) "Chemical oxidation of wastewater from molasses fermentation with ozone," Chemosphere. 51:893-900.

Quennsland Sugar Corporation (Jul. 1997) "Sugar Notes" Brochure. pp. 1-76.

Robertson et al. (Jun. 1978) "The Selective Removal of Final Molasses Components by Ethanolic Precipitation," In; The Proceedings of the South African Sugar Technologists' Association. pp. 85-88.

Rosenberg et al. (1955) "Response of Growing and Mature Pullets to Continuous Feeding of Cane Final Molasses," Hawaii Agricultural Experiment Station Technical Paper No. 349. pp. 292-303.

Saska et al. (2002) "Antioxidant properties of sugarcane extracts", Proceedings of First Biannual World Conference on Recent Developments in Sugar Technologies. 5 pgs.

Saska et al. (2006) "Antioxidants: an excellent phytochemical functional food from sugarcane," Meeting of Sugar Industry Technologists, Inc. Paper No. 898. 23 pgs.

Schoen et al. (2009) "Regulatory effects of a fermented food concentrate on immune function parameters in healthy volunteers," Nutrition. 25:499-505.

Shokuhin to Kaihatus. (2000) 35(6):15-18 . Abstract Only.

Shore et al. (1984) "Factors Affecting White Sugar Colour," Sugar Technology Reviews. 12:1-99.

Sies et al. (2005) "Nutritional, Dietary and Postprandial Oxidative Stress," J. Nutr. 135:969-972.

Silventoinen et al. (2004) "Tends in obesity and energy supply in the WHO MONICA Project," International Journal of Obesity. 28:710-718.

Simonetti et al. (2001) "[11] Caffeic Acid as Biomarker of Red Wine Intake," Methods in Enzymology. 335:122-130.

Singleton et al. (1965) "Colorimetry of Total Phenolics with Phosphomolybdic-Phosphotungstic Acid Reagents," Am. J. Enol. Vitic. 16:144-158.

Staunton et al. (1999) "On-Line Cane Analysis by Near Infra-Red Spectroscopy," Proc. Aust. Soc. Sugar Cane Technol. 21:20-27.

Staunton et al. (2006) "Development of an Online Bagasse Analysis System Using NIR Spectroscopy," Proc. Aust. Soc. Sugar Cane Technol. 28:1-8.

Stracke et al. (2010) "No effect of the farming system (organic/conventional) on the bioavailability of apple (Malus domestica Bork., cultivar Golden Delicious) polyphenols in healthy men: a comparative study," Eur. J. Nutr. 49:301-310.

Tominaga et al. (2006) "Licorice Flavinoid Oil Effects Body Weight Loss by Reduction of Body Fat Mass in Overweight Subjects," J. Health Sci. 52(6):672-683.

Vercellotti et al. (1996) "Components of Molasses: I. Sugarcane Molasses: Factory and Seasonal Variables," Proceedings of the Conference on Sugar Processing Research. 29 pgs.

Actis-Goretta et al. (2006) "Inhibition of angiotensin converting enzyme activity by flavanol-rich foods," J. Agric. Food Chem. 54:229-234.

Aijun et al. (2001) "A Functional Oligosaccharide in Sugar Beet—Raffinose," China Beet & Sugar 3:24-26.

Altukhov et al. (2004) "Changes in Bioenergetic Functions and Performance Capacity of Athletes after Administration of a Polyphenolic Antihypoxic Agent," Human Physiology. 30(2):216-223.

Anderson (2008) "Chromium and polyphenols from cinnamon improve insulin sensitivity," Proceedings of the Nutrition Society. 67:48-53.

Baba et al. (2005) "Absorption, metabolism, degradation and urinary excretion of rosmarinic acid after intake of Peril/a frutescens extract in humans," Eur. J. Nutr. 44:1-9.

Badescu et al. (2005) "Effect of Some Vegetal Polyphenols on the Dislipemia in Experimental *Diabetes Mellitus*," Rom. J. Physiol. 42:103-120.

Balasubramanian et al. (2010) "The Bmi-1 polycomb protein antagonizes the (−)-epigallocatechin-3-gallate-dependent suppression of skin cancer cell survival," Carcinogenesis. 31(3):496-503.

Banini et al. (2006) "Muscadine grape products intake, diet and blood constituents of non-diabetic and type 2 diabetic subjects", Nutrition. 22:1137-1145.

Barclay et al. (2011) "The Australian Paradox: A Substantial Decline in Sugars Intake over the Same Timeframe that Overweight and Obesity Have Increased," Nutrients. 3:491-504.

Basu et al. (2010) "Blueberries Decrease Cardiovascular Risk Factors in Obese Men and Women with Metabolic Syndrome", J. Nutr. 140:1582-1587.

Bento et al. (1997) "Gel Permeation Chromatography of Sugar Materials Using Spectrophotometric and Evaporative Light Scattering Detectors," SIT Poster #722 Publ. Techn. Papers Proc. Ann. Meet. Sugar Industry Technologies 56:383-392.

Bento et al. (1997) "Improved analysis of sugar colorants," Int. Sugar J. 99(1187):555-562.

Bento et al. (1998) "Study of high-molecular weight compounds in sugar using gel-permeation chromatography with an evaporative light scattering detector," Carbohydrate Polymers. 37:257-261.

Berhow et al. (2000) "Characterization and antimutagenic activity of soybean saponins," Mutation Research. 448:11-22.

Bray et al. (1999) "Current and Potential Drugs for Treatment of Obesity," Endocrine Reviews. 20(6):805-875.

Brown et al. (2009) "Effects of dietary supplementation with the green tea polyphenol epigallocatechin-3-gallate on insulin resistance and associated metabolic risk factors: randomized controlled trial," British J. Nutr. 101:886-894.

Bureau of Sugar Experimental Stations (1991) "Method 33: Total Colour (Colour Index)—Determination in Raw Sugar," In; The

(56) References Cited

OTHER PUBLICATIONS

Standard Laboratory Manual for Australian Sugar Mills: vol. 2 Analytical Methods and Tables. BSES Publications. pp. Method 33 p. 1-p. 2.

Burkon et al. (2008) "Quantification of free and protein-bound trans-resveratrol metabolites and identification of trans-resveratrol-C/O-conjugated diglucuronides—Two novel resveratrol metabolites in human plasma," Mol. Nutr. Food Res. 52:549-557.

Cai et al. (2005) "The rice bran constituent tricin potently inhibits cyclooxygenase enzymes and interferes with intestinal carcinogenesis in ApcM mice," Mol. Cancer Ther. 4(9):1287-1292.

Casey et al.(2004) "Development of a robust microtiter plate-based assay method for assessment of bioactivity," J. Microbiological Methods. 58:327-334.—Abstract Only.

Chajuss (2004) "Soy Molasses: Processing and Utilization as a Functional Food," Ch. 10 In; Soybeans as Functional Foods and Ingredients. 9 pgs.

Chou (2004) "Direct Production of Refined Sugar and Value Added Products from Sugar Cane Mills," Sugar Industry Technologists Sixty Third Annual Technical Conference, May 16-19, 2004. Vancouver, Canada. 19 pgs.

Chou et al. (2008) "Sugarcane extract—an Excellent Phytochemical Functional Foods," 40th Mid-Atlantic Regional Meeting of the American Chemical Society, May 17-21. Bayside, New York. 6 pgs.

Clarke et al. (1990) "Polyfructose: a New Microbial Polysaccharide," Ch. 8 In; Carbohydrates as Organic Raw Materials. pp. 169-181.

Coca et al. (2005) "Variables affecting efficiency of molasses fermentation wastewater ozonation," Chemosphere. 60:1408-1415.

Colombo et al. (2005) "Determination of flavonoids in cultivated sugarcane leaves, bagasse, juice and in transgenic sugarcane by liquid chromatography-UV detection," J. Chromatogr. A. 1103(1):118-124.—Abstract Only.

Colombo et al. (2006) "On-line identification of further flavone C- and O-glycosides from sugarcane (*Saccharum officinarum* L., Gramineae) by HPLC-UV-MS," Phytochemical Analysis. 17:337-343.

Dallas et al. (2008) "Lipolytic effect of a polyphenolic citrus dry extract of red orange, grapefruit, orange (SINETROL) in human body fat adipcytes. Mechanism of action by inhibition of cAMP-phosphodiesterase (PDE)," Phytomedicine. 15:783-792.

Dal-Pan et al. (2010) "Resveratrol suppresses body mass gain in a seasonal non-human primate model of obesity," BMC Physiology. 10(11):1-10.

Duarte-Almeida et al. (2006) "Antioxidant Activity of Phenolics Compounds From Sugar Cane (*Saccharum oificinarum* L.) Juice," Plant Foods for Human Nutrition. 61:187-192.

Edye et al. (1998) "The Fate of Soluble Sugarcane Polysaccharides in Sugar Manufacture," Poster Paper In; Proc. 1998 Sugar Proc. Res. Conf., Savannah, Georgia. 463-467.

Fahey et al. (1976) "Influence of molasses lignin-hemicellulose fractions in rat nutrition," The Journal of Nutrition. 106 (10):1447-1451.

Fernandes et al. (2009) "Biosensor for chlorogenic acid based on an ionic liquid containing iridium nanoparticles and polyphenol oxidase," Talanta. 79:222-228.

Frank et al. (2009) "Daily Consumption of an Aqueous Green Tea Extract Supplement Does Not Impair Liver Function or Alter Cardiovascular Disease Risk Biomarkers in Healthy Men," J. Nutr. 139:58-62.

Fujita et al. (2000) "Anti-*Saccharomyces cerevisiae* from edible plants," Book of Abstracts, 219th ACS National Meeting.—Abstract Only.

Fukino et al. (2005) "Randomized Controlled Trial for an Effect of Green Tea Consumption on Insulin Resistance and Inflammation Markers," J. Nutr. Sci. Vitaminol. 55:335-342.

Fukino et al. (2008) "Randomized controlled trial for an effect of green tea-extract powder supplementation on glucose abnormalities," Eur. J. Clinical Nutr. 62:953-960.

Gao et al. (2007) "Value added functional foods from Cms and cane molasses," Sugar Industry Technologists Sixty Six Annual Technical Conference, May 6-9, 2007. Balitmore, Maryland. 9 pgs.

Gekkan Food Chemical. (2001) 17(10):72-81. Abstract Only.

Godshall (2009) "High Molecular Weight Colourants" Sucropedia.com. Accessible on the Internet at URL: http://sucropedia.com. 5 pgs.

Goosens et al. (2003) "Possible involvement of the adipose tissue renin-angiotensin system in the pathophysiology of obesity and obesity-related disorders," Obesity Reviews. 4:43-55.

Han et al. (2003) "Anti-obesity Action of Salix matsudana Leaves (Part 1). Anti-obesity Action by Polyphenols of Salix matsudana in High Fat-diet Treated Rodent Animals," Phytother. Res. 17(10):1188-1194.

Hangyal (1969) "Sugar refining from normal crystals," Cukoripar. 22(4):152-177.—Abstract Only.

Hatano et al. (2008) "Separation and characterization of the colored material from sugarcane molasses," Chemosphere. 71:1730-1737.

Hollis et al. (2009) "Effects of Concord Grape Juice on Appetite, Diet, Body Weight, Lipid Profile, and Antioxidant Status of Adults," J. Am. College Nutr. 28(5):574-582.

Hu et al. "Effects of N, O-carboxymethyl chitosan on abnormality of spermatozoon in mice," Zhonqquo Linchuang Kangfu. 10(43):79-81. (2006)—Abstract Only.

Ishikura et al. (2008) "Safety evaluation of excessive intake of the drink containing Japanese pagoda tree polyphenol (enzymatically modified isoquercitrin) in healthy adults including obesity persons," Japanese Pharmacology & Therapeutics. 36(10):931-939.—Abstract Only.

Islam (2008) "Secondary Metabolites from Nonhost Plants Affect the Motility and Viability of Phytopathogenic Aphanomyces cochlioides Zoospores," Z. Naturforsch. 63(3-4):233-240.

Jacome et al. (2009) "Effects of Green Coffee Bean Extract in Some Biomarkers of Adult Brazilian Subjects," Alim. Nutr. 20(2):185-190.

Johnston et al. (2005) "Dietary polyphenols decrease glucose uptake by human intestinal Caco-2 cells," FEBS Lett. 579:1653-1657.

SEQUENCE LISTING

```
<160> NUMBER OF SEQ ID NOS: 10

<210> SEQ ID NO 1
<211> LENGTH: 22
<212> TYPE: DNA
<213> ORGANISM: Artificial Sequence
<220> FEATURE:
<223> OTHER INFORMATION: Primer

<400> SEQUENCE: 1
ctatgctctc cctcacgcca tc                                             22

<210> SEQ ID NO 2
<211> LENGTH: 21
<212> TYPE: DNA
<213> ORGANISM: Artificial Sequence
<220> FEATURE:
<223> OTHER INFORMATION: Primer

<400> SEQUENCE: 2
ccacgctcgg tcaggatctt c                                              21

<210> SEQ ID NO 3
<211> LENGTH: 22
<212> TYPE: DNA
<213> ORGANISM: Artificial Sequence
<220> FEATURE:
<223> OTHER INFORMATION: Primer

<400> SEQUENCE: 3
gccgcttatg tgtatcgctc ag                                             22

<210> SEQ ID NO 4
<211> LENGTH: 21
<212> TYPE: DNA
<213> ORGANISM: Artificial Sequence
<220> FEATURE:
<223> OTHER INFORMATION: Primer

<400> SEQUENCE: 4
gccagtgctg ccgtcataat g                                              21

<210> SEQ ID NO 5
<211> LENGTH: 24
<212> TYPE: DNA
<213> ORGANISM: Artificial Sequence
<220> FEATURE:
<223> OTHER INFORMATION: Primer
```

-continued

```
<400> SEQUENCE: 5
ggaagccctt tggtgacttt atgg                                              24

<210> SEQ ID NO 6
<211> LENGTH: 22
<212> TYPE: DNA
<213> ORGANISM: Artificial Sequence
<220> FEATURE:
<223> OTHER INFORMATION: Primer

<400> SEQUENCE: 6
gcagcaggtt gtcttggatg tc                                                22

<210> SEQ ID NO 7
<211> LENGTH: 21
<212> TYPE: DNA
<213> ORGANISM: Artificial Sequence
<220> FEATURE:
<223> OTHER INFORMATION: Primer

<400> SEQUENCE: 7
gctggtggtg gtcggagata c                                                 21

<210> SEQ ID NO 8
<211> LENGTH: 24
<212> TYPE: DNA
<213> ORGANISM: Artificial Sequence
<220> FEATURE:
<223> OTHER INFORMATION: Primer

<400> SEQUENCE: 8
cattacgggc aacattggga gaag                                              24

<210> SEQ ID NO 9
<211> LENGTH: 24
<212> TYPE: DNA
<213> ORGANISM: Artificial Sequence
<220> FEATURE:
<223> OTHER INFORMATION: Primer

<400> SEQUENCE: 9
ggttctagcc agcagagtct acag                                              24

<210> SEQ ID NO 10
<211> LENGTH: 23
<212> TYPE: DNA
<213> ORGANISM: Artificial Sequence
<220> FEATURE:
<223> OTHER INFORMATION: Primer

<400> SEQUENCE: 10
ctcgttgtca catcagccac ttg                                               23
```

SUGAR EXTRACT

RELATED APPLICATIONS

This application is a divisional of U.S. application Ser. No. 15/380,388, filed on Dec. 15, 2016, which is a divisional of U.S. application Ser. No. 13/984,328, filed on Aug. 15, 2014, now issued as U.S. Pat. No. 9,572,852, which is a 35 U.S.C. § 371 filing of International Application No. PCT/AU2012/000115, filed Feb. 8, 2012, all of which are incorporated herein by reference in their entireties.

FIELD OF THE INVENTION

The invention relates to extracts produced from sugar cane and sugar beet waste processing stream products having desirable properties and health benefits. More particularly the invention relates to hydrophobic extracts obtained from molasses, methods of producing the extracts, uses of the extracts, and products containing the extracts.

BACKGROUND OF THE INVENTION

Sugar is a common carbohydrate sourced from sugar cane and sugar beet used in food because of its sweet taste. Ordinary table sugar (sucrose) is a disaccharide made up of one molecule of glucose bound by a α-1,2-glycoside to one molecule of fructose. Table sugar is 99.5% sucrose, the most biologically abundant disaccharide. Saccharides are simple carbohydrates classified as monosaccharides, oligosaccharides or polysaccharides depending upon their structure. Sucrose is sourced from both sugarcane and beets.

i) Sugar Processing

The processing steps required to produce white sugar result in generation of a number of byproducts, most of which are considering waste products with little or no nutritional value or use in human applications.

After being mechanically harvested, sugar cane is transported to a mill and crushed between serrated rollers. The crushed sugar cane is then pressed to extract the raw sugar juice, while the bagasse (leftover fibrous material) is used for fuel. The raw juice is then heated to its boiling point to extract any impurities and lime and bleaching agents are added and mill mud is removed. The raw juice is further heated under vacuum to produce bulk sugar crystals and a thick syrup known as molasses. The two are separated by a centrifuge and the molasses waste stream is collected for use as a low-grade animal feedstock. The bulk sugar crystals are further refined to increase their purity.

The bulk sugar crystals from the above process are further refined to produce the many commercially available sugar products. The bulk sugar crystals are mixed with a hot concentrated syrup to soften the outer coating on the crystals. The crystals are recovered by centrifuge and then dissolved in hot water. This sugar liquor is then further purified by carbonation or phosfloatation, filtration, decolourisation and then seeded with fine sugar crystals. Once the crystals have grown to the requisite size, the crystals are separated from the syrup by centrifuge, dried, graded and then packaged. There may be several repetitions of recovering sugar crystals from the sugar liquor. The dark sugar syrup which is left after all of the sugar crystals have been recovered is also called molasses.

Approximately 70% of the world's sugar comes from sugar cane and about 30% comes from sugar beets similar processes are used to manufacture sugar products from sugar beets. However, it is a single step rather than two step process.

The processing starts by slicing the beets into thin strips/chips/cossettes. This process increases the surface area of the beet to make it easier to extract the sugar. The extraction takes place in a diffuser where the beet is kept in contact with hot water and the resultant sugar solution is referred to as the juice. The exhausted beet slices from the diffuser are then pressed to squeeze as much juice as possible out of them. The pressed beet, by now a pulp, is sent to drying plant where it is turned into pellets which form an important constituent of some animal feeds. The juice is then cleaned up before it can be used for sugar production and the non-sugar chemicals are removed in a process called carbonation (milk of lime (calcium hydroxide) and carbon dioxide gas). The calcium carbonate (chalk) which forms traps the non-sugar chemicals and is removed (called mud) in the clarifier. Once this is done the sugar liquor is concentrated until sugar crystals form. Once the crystals have grown the resulting mixture of crystals and mother liquor is spun in centrifuges to separate the two. The crystals are then given a final dry with hot air before being packed and/or stored ready for dispatch. The final sugar is white and ready for use. Because one cannot get all the sugar out of the juice, there is a sweet by-product made: beet molasses. This is usually turned into a cattle food or is sent to a fermentation plant such as a distillery where alcohol is made.

ii) Polyphenols, Polyphenol Glycosides and Phenolic Acids

Polyphenols (compounds with two or more phenol groups) are a class of phytochemicals found in a variety of sources including wine, grapes, cocoa and sugar cane and sugar beet. Natural polyphenols can range from simple molecules such as phenolic acids to large highly polymerized compounds such as tannins Polyphenols (or phenolics) all have a common basic chemical component, that is, a phenolic ring structure. There are at least 8000 identified polyphenols in a number of subcategories, such as anthocyanins and catechins. Polyphenols can exist in their free form, or as polyphenol glycosides.

Conjugated forms of polyphenols are the most common, where various sugar molecules, organic acids and lipids (fats) are linked with the phenolic ring structure. Despite having a common phenolic ring structure, differences in the conjugated chemical structure, size and other substituents account for different chemical classifications and significantly, variation in the modes of action and health properties of the various compounds.

Phenolic acids are simple molecules such as caffeic acid, vanillin, and coumaric acid. Phenolic acids form a diverse group that includes the widely distributed hydroxybenzoic and hydroxycinnamic acids (despite the latter two only having one phenolic ring). Hydroxycinnamic acid compounds (p-coumaric, caffeic acid, ferulic acid) occur most frequently as simple esters with hydroxy carboxylic acids or glucose, while the hydroxybenzoic acid compounds (p-hydroxybenzoic, gallic acid, ellagic acid) are present mainly in the form of glucosides. Coffee is particularly rich in bound phenolic acids, such as caffeic acid, ferulic acid, and p-coumaric acid.

Reference to any prior art in the specification is not, and should not be taken as, an acknowledgment or any form of suggestion that this prior art forms part of the common general knowledge in Australia or any other jurisdiction or that this prior art could reasonably be expected to be ascertained, understood and regarded as relevant by a person skilled in the art.

SUMMARY OF THE INVENTION

The invention relates to hydrophobic extracts obtained from molasses, methods of producing the extracts, uses of the extracts, and products containing the extracts. In one aspect of the invention, there is provided a molasses extract with a high relative abundance of hydrophobic compounds including polyphenols. Ie a molasses extract enriched with hydrophobic compounds including polyphenols compared to molasses itself. More particularly, there is provided a molasses extract with a high relative abundance of hydrophobic compounds including polyphenols wherein the extract comprises at least 9000 mg CE/100 g of hydrophobic polyphenols in a mixture of free form polyphenols selected from apigenin, catechin, catechin gallate, epicatechin, kaempherol, luteolin, quercetin, tricin, myricetin and diosmetin; polyphenol glycosides selected from diosmin, tricin-7-O-neohesperidoside, orientin, vitexin, luteolin-8-C-(rhamnosylglucoside), schaftoside, isoschaftoside, and rutin; and phenolic acids, selected from caffeic acid, chlorogenic acid, p-coumaric acid, ferulic acid, gallic acid, syringic acid, and vanillic acid;

trace elements selected from one or more of calcium, iron, magnesium, manganese, potassium and sodium;

protein and other nitrogen-containing compounds; and carbohydrates other than monosaccharides and sucrose wherein the extract has less than 2 g of monosaccharides and sucrose per 100 g of extract.

Preferably the hydrophobic polyphenols are present in an amount of at least 18000 mg CE/100 g of extract, more preferably at least 21000 CE/100 g extract, and the extract comprises a combination of all of apigenin, catechin, catechin gallate, epicatechin, kaempherol, luteolin, quercetin, tricin, myricetin, diosmetin, diosmin, tricin-7-O-neohesperidoside, orientin, vitexin, luteolin-8-C-(rhamnosylglucoside), schaftoside, isoschaftoside, rutin, caffeic acid, chlorogenic acid, p-coumaric acid, ferulic acid, gallic acid, syringic acid, and vanillic acid.

Extracts of the invention can be produced by contacting molasses with a hydrophobic polymeric adsorbent to bind compounds including polyphenols in the molasses. In this aspect of the invention, there is provided a method for producing a molasses extract with a high relative abundance of hydrophobic compounds including polyphenols, comprising the steps of:

a. contacting a sample of molasses with a hydrophobic polymeric adsorbent under conditions sufficient to enable binding of compounds to the adsorbent; and b. eluting the bound compounds wherein the eluted product from step (b) has a high relative abundance of hydrophobic compounds including polyphenols compared to the sample of molasses ie prior to step (a).

More particularly, there is provided a method for producing a molasses extract of the invention with a high relative abundance of hydrophobic compounds including polyphenols comprising the steps of:

a. diluting the molasses to produce a 10 to 40% w/v aqueous solution;

b. optionally filtering the diluted molasses produced in step (a);

c. contacting the diluted molasses with a hydrophobic polymeric adsorbent under conditions sufficient to enable binding of compounds to the adsorbent and flow through of all other compounds in the diluted molasses;

d. optionally passing the flow through from step (c) over the hydrophobic polymeric adsorbent at least once;

e. optionally rising the hydrophobic polymeric adsorbent; and f. eluting the compounds bound to the hydrophobic polymeric adsorbent to produce the extract wherein the compounds are eluted with 30 to 70% ethanol, preferably 40% ethanol.

The extract has a high relative abundance of hydrophobic compounds including polyphenols compared to the sample of molasses used as the starting material.

There is also provided a molasses extract with a high relative abundance of hydrophobic compounds including polyphenols obtained from the method of the invention.

In another aspect of the invention, the extracts of the invention can be formulated in to a therapeutic composition for use in a number of therapeutic methods. In one embodiment there is provided a method for decreasing body fat and/or minimising fat accumulation in an animal by administering a composition including a molasses extract having a relatively high abundance of hydrophobic compounds including polyphenols in an amount effective to decrease total body fat and/or minimise fat accumulation of the animal.

In a further embodiment, there is provided a method of reducing energy absorption and/or altering fat metabolism by administering a composition including a molasses extract having a relatively high abundance of hydrophobic compounds including polyphenols in an amount effective to reduce energy absorption and/or alter fat metabolism.

Methods of alleviating or reducing the severity of fatigue, and methods of improving and elevating energy levels in an animal by administering a composition including a molasses extract having a relatively high abundance of hydrophobic compounds including polyphenols in an amount effective are also contemplated.

In a further embodiment, there is provided a method of improving postprandial satiety in an individual by administering a composition including a molasses extract having a relatively high abundance of hydrophobic compounds including polyphenols in an amount effective to decrease a desire to have further food.

As an alternative to administering a composition, the individual may be administered the extract of the invention as part of a satiety inducing food.

There is also provided use of an effective amount of a molasses extract having a relatively high abundance of hydrophobic compounds including polyphenols in the preparation of medicament for decreasing body fat, minimising fat accumulation, reducing energy absorption and/or altering fat metabolism, improving and elevating energy levels in an animal, and improving postprandial satiety.

In a further embodiment, there is provided an effective amount of a molasses extract having a relatively high abundance of hydrophobic compounds including polyphenols for decreasing body fat, minimising fat accumulation, reducing energy absorption and/or altering fat metabolism, improving and elevating energy levels in an animal, and improving postprandial satiety.

The invention also provides a composition for decreasing body fat, minimising fat accumulation, reducing energy absorption and/or altering fat metabolism, improving and elevating energy levels in an animal, and improving postprandial satiety, the composition comprising as an active ingredient a molasses extract having a relatively high abundance of hydrophobic compounds including polyphenols.

Another aspect of the present invention includes food products comprising an extract according to the invention alone as the active ingredient or in combination with other active ingredients.

In yet another embodiment, there is provided a satiety inducing food including a molasses extract having a relatively high abundance of hydrophobic compounds including polyphenols.

In yet another embodiment, there is provided a pet food including a molasses extract having a relatively high abundance of hydrophobic compounds including polyphenols, wherein the pet food is preferably for companion animals including cats, dogs and horses.

In each of these embodiments, the molasses extract of the invention is preferably produced by the methods of the invention. These and other aspects of the invention will now be described in greater detail.

DETAILED DESCRIPTION OF THE EMBODIMENTS

Figure 1A:
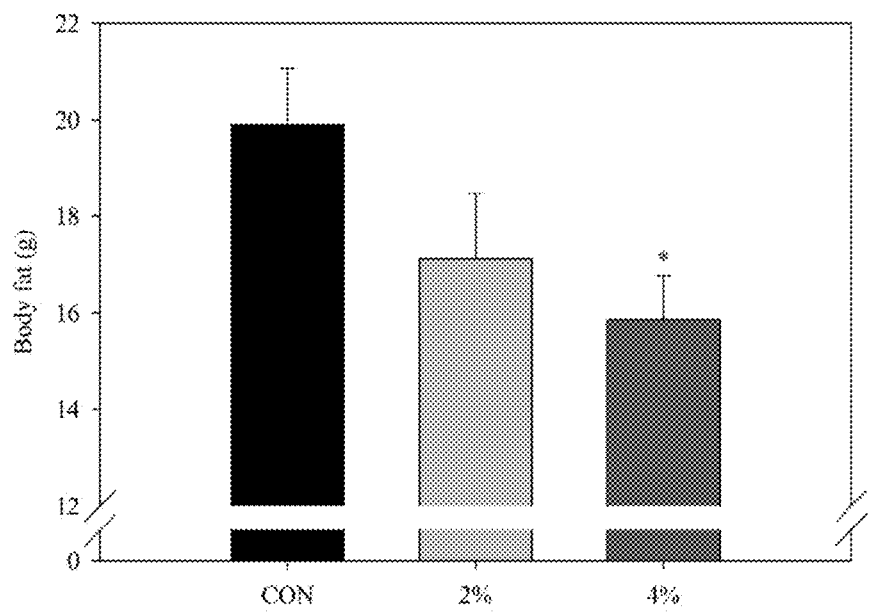
FIG. 1A: Mean differences (±SEM) in fat mass between the three experimental groups. * p<0.05—denotes significant difference from the control group. (CON—control; 2%-2% extract; 4%-4% extract).
Figure 1B:
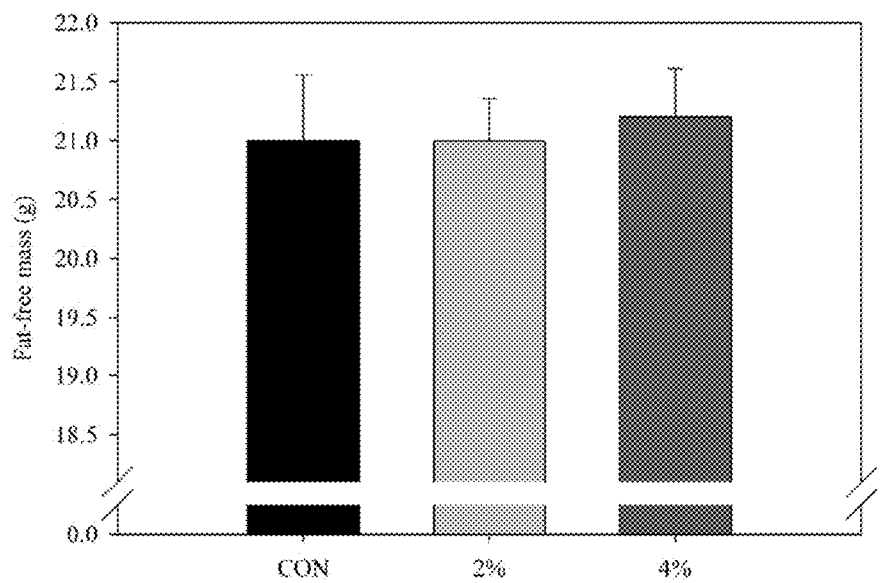
FIG. 1B: Mean differences (±SEM) in fat-free mass between the three experimental groups. (CON—control; 2%-2% extract; 4%-4% extract).

Polyphenols are a class of phytochemicals found in a variety of sources including wine, grapes, cocoa, tea and sugar cane or sugar beet. However the inventors are the first to recognise that hydrophobic molecules including particular hydrophobic polyphenols and their glycosides, as well as phenolic acids, derived from sugar cane or beet waste stream products such as molasses, have specific health benefits.

i) High Polyphenol and Phenolic Acids Containing Molasses Extract and Method of its Production The inventors have found that the retentate obtained by subjecting molasses derived from sugar cane or sugar beet to hydrophobic polymeric adsorbance is enriched in hydrophobic molecules, particularly hydrophobic polyphenols and their glycosides, as well as phenolic acids. Therefore, in one aspect of the invention, there is provided a molasses extract with a high relative abundance of hydrophobic compounds including polyphenols.

By the phrase "hydrophobic compounds" it is intended to refer to compounds with sufficient hydrophobicity to bind to a hydrophobic polymeric adsorbant. Such compounds will have varying degrees of water solubility, and as would be appreciated and understood by those skilled in the art, sufficient hydrophobicity would equate to a compound that binds to a hydrophobic adsorbent and must be eluted off. Ie the compound would not be removed by washing the adsorbent.

By the phrase "high relative abundance of hydrophobic compounds including polyphenols" it is meant that the level of hydrophobic compounds including polyphenols is enhanced or enriched, such that the molasses extract of the invention has a higher relative abundance of hydrophobic compounds, and in particular polyphenols, compared to molasses prior to processing of the molasses over a polymeric adsorbant. "Polyphenols" is intended to encompass free forms of polyphenols, polyphenol glycosides, and phenolic acids as referred to in more detail throughout the specification.

Preferably, in relation to the hydrophobic polyphenols within the extract, the relative abundance of hydrophobic polyphenols is increased by at least 5 fold, preferably by at least 7 fold, and most preferably by at least 10 fold. This includes, as noted above, the free form polyphenols, polyphenol glycosides and phenolic acids. For example, molasses, prior to being processed over a polymeric adsorbant has approximately polyphenols in an amount of 1800-2100 mg CE/100 g of molasses. The extract of the invention therefore preferably has hydrophobic polyphenols in an amount of at least 9000 mg CE/100 g, more preferably at least 18000 mg CE/100 g, and most preferably at least 21000 mg CE/100 g. "CE", or "catechin equivalent" is a measure of total polyphenolic content, expressed as mg catechin equivalents/g crude material.

As used herein, the term "molasses" refers to the dark syrup which is left behind after the bulk sugar crystals are collected in the sugar cane mill, the black syrup remaining after the sugar cane syrup has been centrifuged for the last time in the refinery or beet molasses. Preferably, the molasses used is from the sugar cane mill.

The extracts of the present invention represent new products which are economically useful and can be used in a wide variety of applications. Accordingly, in another aspect of the invention, there is provided a therapeutic composition including a molasses extract with a high relative abundance of hydrophobic compounds including polyphenols and a pharmaceutically acceptable carrier, excipient or diluent.

The term "therapeutic composition" is a broad term which includes enteral and parenteral pharmaceutical preparations, nutraceuticals, supplements, functional foods and herbal preparations, some of which are described in more detail below. Examples of suitable formulations include tablets, powders, chewable tablets, capsules, oral suspensions, suspensions, emulsions or fluids, children's formulations, enteral feeds, nutraceuticals, suppositories, nasal sprays, drinks and food products. The carrier may contain any suitable excipients such as starch or polymeric binders, sweeteners, colouring agents, emulsifiers and coatings. Preferably, the carrier is a food product or food ingredient such as sugar.

The therapeutic composition may be in any form appropriate for administration to the subject. The therapeutic composition may be administered topically, orally or by any other route of administration.

The compositions and methods of the present invention have applications in human medicine, the cosmetic and aesthetic industries, veterinary medicine as well as in general, domestic and wild animal husbandry. The term "animal" as used herein therefore refers to any animal. Preferably, the animal is a mammal and more preferably a human. An "animal" also includes livestock species such as cattle, horses, sheep, pigs, goats, donkeys and poultry birds such as chickens, ducks, turkeys and geese or domestic animals such as cats and dogs. An animal, regardless of whether a human or non-human animal, may also be referred to as an individual, subject, patient, host or recipient.

While there are methods in the art which subject sugar cane or sugar beet products to extraction and purification processes, the skilled person will appreciate that, depending on the purification/extraction/treatment process used, the polyphenol composition of an end product will vary. For the first time, this application describes a method involving the step of passing molasses over a hydrophobic polymeric adsorbe dance with the figure below) to produce the extract of the invention having a higher relative abundance of hydrophobic compounds including polyphenols compared to molasses that has not been exposed to a polymeric adsorbant.

In one embodiment of this aspect of the invention there is provided a method for producing a molasses extract with a high relative abundance of hydrophobic compounds including polyphenols, comprising the steps of:
 a. contacting a sample of molasses with a hydrophobic polymeric adsorbent under conditions sufficient to enable binding of compounds to the adsorbent; and
 b. eluting the compounds
wherein the eluted product from step (b) has a high relative abundance of hydrophobic compounds including polyphenols compared to the sample of molasses. In other words, the eluted product from step (b) has a high relative abundance of hydrophobic compounds including polyphenols compared to the sample of molasses prior to step (a). Preferably the hydrophobic compounds are eluted with 30 to 70% ethanol, most preferably 40% ethanol.

As used herein, except where the context requires otherwise, the term "comprise" and variations of the term, such as "comprising", "comprises" and "comprised", are not intended to exclude further additives, components, integers or steps.

Preferably the hydrophobic polyphenols within the extract are at least 5 to 10 fold higher than the molasses prior to processing over a polymeric adsorbent, and are present in amounts of at least 9000 mg CE/100 g, more preferably at least 18000 mg CE/100 g, and most preferably at least 21000 mg CE/100 g of molasses extract.

Preferably the hydrophobic polymeric adsorbent is a polystyrene, non-ionic, hydrophobic, cross-linked polymer, containing both a continuous polymer phase and continuous pore phase, and can be used in batch or column form. This enables isolation of compounds of sufficient hydrophobicity to bind to the hydrophobic adsorbent, including polyphenols from the molasses. Preferably, large scale methods utilise column (ie fixed bed) modes. A useful polymeric adsorbent for use in the invention is Amberlite™ XAD16N™. It is preferred that the polymeric adsorbent be food grade, particularly food grade for human use. A useful food grade polymeric adsorbent is Amberlite™ FPX66™.

Molasses from sugar cane or sugar beet is mixed with an aqueous solution, preferably water, to form a diluted molasses solution. Preferably the molasses is a 10 to 40% w/v solution, and more preferably approx. a 20% w/v solution. Sediment and undissolved matter can optionally be removed from the diluted molasses solution, either by centrifugation, or more preferably, by filtration through an appropriate sized filter. 0.1 µM stainless steel filters are one such option although the skilled person will be aware of other suitable filters in the art. The diluted molasses is then contacted with the polymeric adsorbent under conditions sufficient to enable binding of the hydrophobic compounds to the adsorbent. Typically the molasses sample is loaded on to the column at a flow rate of 2 to 6 L/min, preferably 4 L/min. It is also possible to define an extraction process by virtue of the length of time the sample is left in contact with the adsorbent. Preferably, in one embodiment, the diluted molasses is left in contact with the polymeric adsorbant for a period of 30-120 minutes, and preferably at least about 60 minutes, at ambient temperature. After the first flow through, the molasses can optionally be cycled across the resin in the column at least once more, preferably twice, for a total of 3 cycles.

Following optional rinsing steps of the adsorbant with an aqueous solution such as water, the retentate is then eluted, preferably with an alcohol, to produce the molasses extract of the invention having a high relative abundance of hydrophobic compounds including polyphenols. 30 to 80% v/v ethanol is one suitable alcohol for use in eluting the retentate, passed over the column at a flow rate of 2 to 6 L/min, preferably 4 L/min. The elution step can also be defined by virtue of time. Preferably, in one embodiment, the ethanol can be mixed with the adsorbent for a period of 2-15 minutes to ensure as much desorption of the hydrophobic compounds off the adsorbent as possible. 30 to 70% ethanol is used, preferably 40% ethanol.

The extract obtained from the elution step can be concentrated by flash evaporation. It will be within the scope of the skilled person in the art to determine suitable conditions for evaporation. Suitable exemplary conditions for evaporation include:

feed flow rate: 150-200 L/hr; preferably about 180 L/hr
feed preheat temperature: 40-50° C.; preferably about 45° C.
recycle rate: 180-200 L/hr; preferably about 195 L/hr
operating vacuum: 5-10 $kPa_{abs}$; preferably about 8 $kPa_{abs}$
vessel temperature: 30-40° C.; preferably about 32-36° C.

There is therefore provided a method for producing a molasses extract with a high relative abundance of hydrophobic compounds including polyphenols at levels 5 to 10 fold higher than molasses, comprising the steps of:
a. diluting the molasses to produce a 10 to 40% w/v aqueous solution;
b. optionally filtering the diluted molasses produced in step (a);
c. contacting the diluted molasses with a hydrophobic polymeric adsorbent under conditions sufficient to enable binding of compounds to the adsorbent and flow through of all other compounds in the diluted molasses;
d. optionally passing the flow through from step (c) over the hydrophobic polymeric adsorbent at least once;
e. optionally rising the hydrophobic polymeric adsorbent; and
f. eluting the compounds bound to the hydrophobic polymeric adsorbent to produce the extract wherein the extract produced in step (f) has a high relative abundance of hydrophobic compounds including polyphenols levels 5 to 10 fold higher than the sample of molasses prior to it being subjected to steps (b) to (f). Preferably the hydrophobic compounds are eluted with 30 to 70% ethanol, most preferably 40% ethanol, and the molasses extract contains hydrophobic polyphenols in an amount of at least at least 9000 mg CE/100 g, more preferably at least 18000 mg CE/100 g, and most preferably at least 21000 mg CE/100 g.

This method produces a concentrated extract suitable for freeze drying.

Other than optionally filtering the molasses for the purpose of removing sediment and undissolved matter in step (b), this method of producing an extract does not subject the molasses to any pre-treatment steps to remove other substances prior to exposing the molasses to the polymeric adsorbent. Prior art methods subject polyphenol containing substances to other purification and filtration steps to remove the higher molecular weight compounds and polyphenols, which impart undesirable colour and taste to the substance. The method of the invention does not include any steps for the specific purpose of removing these polyphenols or other components, and the extract of the invention generated by hydrophobic polymeric adsorption of molasses retains a number of these polyphenols. There is therefore provided a method for producing a molasses extract with a high relative abundance of hydrophobic compounds including polyphenols at levels 5 to 10 fold higher than molasses, wherein the molasses is not subject to any pre-treatment steps prior to contacting the molasses with the hydrophobic polymeric adsorbent that would remove high molecular weight compounds including high molecular weight polyphenols (other than in sediment or undissolved matter mentioned above). Put another way, the molasses, or the diluted molasses used in the method of the invention to produce a molasses extract with a high relative abundance of hydrophobic compounds is untreated molasses, which has not been treated to remove high molecular weight compounds.

In a further embodiment of the invention, there is also provided an extract from molasses with a high relative abundance of hydrophobic compounds including polyphenols when produced by a method of the invention.

In an alternative method of producing an extract from molasses with a high relative abundance of hydrophobic compounds including polyphenols, the hydrophobic compounds may be removed from molasses using a selective absorption process, whereby hydrophobic compounds, including polyphenols, are extracted using suitable solvents. Suitable solvents include but are not limited to ethanol, methanol, acetone and ethyl acetate, or mixtures thereof, and dilutions thereof such as 50/50 ethanol/water. The solvent containing the polyphenols may then be subjected to additional purification steps to remove any solid matter, prior to vacuum evaporation to produce the extract.

ii) Characterisation of Molasses Extract

The molasses extract of the invention contains hydrophobic polyphenols in an amount of at least 9000 mg CE/100 g, more preferably at least 18000 mg CE/100 g, and most preferably at least 21000 mg CE/100 g. As explained earlier, "CE", or "catechin equivalent" is a measure of total polyphenolic content, expressed as mg catechin equivalents/g crude material.

The polyphenols in the molasses extract of the invention can be polyphenols in free form or as a glycoside or can be a phenolic acid. For example, the molasses extract may include one or more of the following polyphenols, polyphenol glycosides and phenolic acids:

free form polyphenols selected from one or more of apigenin, catechin, catechin gallate, epicatechin, kaempherol, diosmin, luteolin, quercetin, tricin, myricetin and diosmetin;

polyphenol glycosides selected from one or more of diosmin, tricin-7-O-neohesperidoside, orientin, vitexin, luteolin-8-C-(rhamnosylglucoside), schaftoside, isoschaftoside, rutin; and phenolic acids, selected from one or more of caffeic acid, chlorogenic acid, p-coumaric acid, ferulic acid, gallic acid, syringic acid, and vanillic acid.

Accordingly, in one embodiment of the invention, there is provided a molasses extract having a relatively high abundance of hydrophobic compounds including polyphenols, wherein the polyphenols are present in a mixture of:

free form polyphenols selected from one or more of apigenin, catechin, catechin gallate, epicatechin, kaempherol, diosmin, luteolin, quercetin, tricin, myricetin and diosmetin;

polyphenol glycosides selected from one or more of diosmin, tricin-7-O-neohesperidoside, orientin, vitexin, luteolin-8-C-(rhamnosylglucoside), schaftoside, isoschaftoside, rutin;

and phenolic acids, selected from one or more of caffeic acid, chlorogenic acid, p-coumaric acid, ferulic acid, gallic acid, syringic acid, and vanillic acid, and are present in an amount of at least 9000 mg CE/100 g, or at least 18000 mg CE/100 g, or at least 21000 mg CE/100 g.

Preferably, the free form polyphenols are at least catechin, epicatechin, and quercetin, the polyphenol glycoside is diosmin, and the phenolic acids are at least caffeic acid, chlorogenic acid, p-coumaric acid, ferulic acid, and syringic acid. More preferably, catechin is present in the amount of 150 to 200 mg/kg, epicatechin is present in the amount of 150 to 220 mg/kg, quercetin is present in the amount of 80 to 150 mg/kg, diosmin is present in the amount of 410 to 425 mg/kg, caffeic acid is present in the amount of 100 to 320 mg/kg, chlorogenic acid is present in the amount of 100 to 400 mg/kg, p-coumaric acid is present in the amount of 1100 to 1300 mg/kg, ferulic acid is present in the amount of 700 to 760 mg/kg, and syringic acid is present in the amount of 400 to 500 mg/kg.

Polyphenol glycosides may be O linked or C linked glycosides. O-glycosides, such as diosmin, tricin, and rutin are hydrolysable, and are broken down either by bacterial enzymes in the intestine, or human enzymes in the intestinal cell wall to unconjugated polyphenol aglycones which are very easily absorbed. However, prior to absorption, the aglycones can be conjugated with glucuronic acid, such that very little unconjugated polyphenol is actually absorbed.

The C-glycosides however, including those that lose the O-glycoside moiety to expose the C-glycoside part of the molecule, have a C—C bond that is not hydrolysable by enzymes or acids. C-glycosides therefore remain intact, and without being bound to any theory, can behave as substrates for the glucose transporters in the intestine and kidney, thereby blocking glucose transport. Orientin, vitexin, luteolin-8-C-(rhamnosylglucoside), schaftoside and isoschaftoside are all C-glycosides. Accordingly, in one embodiment of the invention, the molasses extract is enriched for C-glycosides, including but not limited to orientin, vitexin, luteolin-8-C-(rhamnosylglucoside), schaftoside and isoschaftoside.

The molasses extract of the invention having a relatively high abundance of hydrophobic compounds including polyphenols, in an amount of at least of at least 9000 mg CE/100 g, or at least 18000 mg CE/100 g, or at least 21000 mg CE/100 g, also contains trace elements, carbohydrates including small amounts of sugars, moisture, ash and protein.

The molasses extract of the invention preferably contains the following trace elements, shown as element (mg) per weight of extract.

TABLE 1

| Trace Element | Concentration range | Preferred concentration |
| --- | --- | --- |
| Calcium | 8000-9000 mg/kg | 8800 mg/kg |
| Iron | 800-1000 mg/kg | 860 mg/kg |
| Magnesium | 1500-2500 mg/kg | 2000 mg/kg |
| Manganese | 50-100 mg/kg | 65 mg/kg |
| Potassium | 100-250 mg/kg | 190 mg/kg |
| Sodium | 10-50 mg/100 g | 30 mg/100 g |

The molasses extract of the invention also preferably contains no or minimal monosaccharide and disaccharide sugars. By "minimal sugars" it is meant that the total of fructose, glucose, sucrose, maltose, lactose and maltotriose is less than 2 g per 100 g of extract, and preferably less than 1 g per 100 g of extract as per the following:

TABLE 2

| Sugars | Concentration |
| --- | --- |
| Fructose | <0.2 g/100 g |
| Glucose | <0.2 g/100 g |
| Sucrose | 0.3 g/100 g |
| Maltose | <0.2 g/100 g |
| Lactose | <0.2 g/100 g |
| Maltotriose | <0.2 g/100 g |
| Total Sugars | <1 g/100 g |

The molasses extract of the invention contains no detectable fat, or fatty acids present in an amount above 0.1 g/100 g of extract. The extract is also low in moisture. By "low in moisture" it is meant that there is less than 10 g of moisture per 100 g extract, or less than 10%, and preferably less than 6 g/100 g extract, or less than 6%.

The molasses extract of the invention may also contain ash, in an amount of 1 to 5 g of ash per 100 g of extract, preferably 2.5 g to 3.5 g of ash per 100 g of extract.

By detecting nitrogen, it is possible to determine protein content of the molasses extract of the invention. In this regard, the protein content was estimated to be 5 to 20 g/100 g of extract, preferably 10 to 15 g/100 g of extract and most preferably 12 to 13 g/100 g of extract. Other than protein, other N-containing compounds present in the extract may be alkaloids.

Carbohydrates other than monosaccharides and sucrose are present in an amount of approximately 25 to 50 g/100 g of the extract, preferably 30 to 40 g/100 g.

While the mono and disaccharide content of the molasses extract is less than 2 g per 100 g of extract, and preferably less than 1 g per 100 g of extract, polymeric glycosyl residues are contained within the extract and form part of the carbohydrate content of the molasses extract as per the following:

TABLE 3

| Glycosyl residue: | Mass/300 ug | Mol %[1] |
| --- | --- | --- |
| Arabinose (Ara) | 0.6 | 0.6 |
| Rhamnose (Rha) | 0.8 | 0.8 |
| Fucose (Fuc) | n.d. | — |
| Xylose (Xyl) | 0.9 | 0.9 |
| Glucuronic Acid (GlcA) | n.d. | — |
| Galacturonic acid (GalA) | n.d. | — |
| Mannose (Man) | 0.2 | 0.1 |
| Galactose (Gal) | 0.1 | 0.1 |
| Glucose (Glc) | 112.2 | 97.5 |
| N-Acetyl Galactosamine (GalNAc) | n.d. | — |

TABLE 3-continued

| Glycosyl residue: | Mass/300 ug | Mol %[1] |
|---|---|---|
| N-Acetyl Glucosamine (GlcNAc) | n.d. | — |
| N-Acetyl Mannosamine (ManNAc) | n.d. | — |
| TOTAL | 114.7 | |

[1]Values are expressed as mole percent of total carbohydrate. The total percentage may not add to exactly 100% due to rounding;
n.d = not detected The extract of the invention therefore preferably comprises about 25 to 50 g/100 g of extract, preferably about 30 to 40 g/100 g, of which more than 90% is polymers of glucose residues (not free glucose).

Accordingly, in one embodiment of the invention, there is provided a molasses extract with a high relative abundance of hydrophobic compounds including polyphenols present in an amount of at least 9000 mg CE/100 g, or at least 18000 mg CE/100 g, or at least 21000 mg CE/100 g, and further comprising one or more of:

trace elements selected from one or more of calcium, iron, magnesium, manganese, potassium and sodium;
protein and other nitrogen-containing compounds; and
carbohydrates other than monosaccharides and sucrose
wherein the extract has less than 2 g of monosaccharides and sucrose per 100 g of extract.

More preferably there is provided a molasses extract with a high relative abundance of hydrophobic compounds including polyphenols wherein the extract comprises at least 9000 mg CE/100 g of hydrophobic polyphenols in a mixture of free form polyphenols selected from apigenin, catechin, catechin gallate, epicatechin, kaempherol, luteolin, quercetin, tricin, myricetin and diosmetin; polyphenol glycosides selected from diosmin, tricin-7-O-neohesperidoside, orientin, vitexin, luteolin-8-C-(rhamnosylglucoside), schaftoside, isoschaftoside, and rutin; and phenolic acids, selected from caffeic acid, chlorogenic acid, p-coumaric acid, ferulic acid, gallic acid, syringic acid and vanillic acid;

trace elements selected from one or more of calcium, iron, magnesium, manganese, potassium and sodium;
protein and other nitrogen-containing compounds; and
carbohydrates other than monosaccharides and sucrose
wherein the extract has less than 2 g of monosaccharides and sucrose per 100 g of extract.

Preferably, the hydrophobic polyphenols are present in an amount of at least 18000 mg CE/100 g, or at least 21000 mg CE/100 g.

In each of the embodiments described above that contain trace elements, the trace elements that are present are present in the amounts of 8000-9000 mg calcium/kg of extract, 800-1000 mg of iron/kg of extract, 1500-2500 mg of magnesium/kg of extract, 50-100 mg of potassium/kg of extract, 100-250 mg of potassium/kg extract and 10-50 mg sodium/100 g of extract. In the embodiments that contain protein and N-containing compounds such as alkaloids, the protein and N-containing compounds are present in an amount of 1 to 15 g of protein and N-containing compounds/100 g of extract.

The carbohydrate component of each of the embodiments described above is 25 g to 50 g/100 g of extract, preferably 30 to 40 g/100 g, and of that, more than 90% is polymeric glucose residues.

The molasses extract of the invention with a high relative abundance of hydrophobic compounds including polyphenols has a high Oxygen Radical Absorbance Capacity (ORAC) value. The ORAC value was calculated by the method described in Cao G, Alessio H, Cutler R (1993). "Oxygen-radical absorbance capacity assay for antioxidants". *Free Radic Biol Med* 14 (3): 303-11. Raw bran is reported to be one of the best antioxidant food products with an ORAC value of 312400 μmol TE/100 g. The molasses extract of the invention, having a total ORAC value in the range of 350000 to 385000 μmol TE/100 g, is at least 20% higher.

iii) Use of the Molasses Extract

As mentioned above, the inventors have found that administration of the extract of the invention can achieve important physiological effects and important health outcomes for the individual to which the extract is administered. The extracts as described herein may be used in a therapeutic capacity in order to treat and/or prevent a number of conditions.

Earlier work by the applicants showed that administration of a molasses filtration extract to an animal was able to alter the distribution of body mass by increasing the proportion of lean mass to fat mass when compared to the consumption of the same food without the addition of these compounds. These body mass altering compounds include polyphenols and milk bioactives (WO2006/128259). In the current application, it has been found that the molasses extract of the invention having a relatively high abundance of hydrophobic compounds including polyphenols can reduce overall body fat and/or minimise fat accumulation by increasing energy excretion and/or by influencing mechanisms involved in fat and sugar oxidation and insulin sensitivity.

Accordingly, in one aspect of the invention, there is provided a method for decreasing body fat and/or minimise fat accumulation in an animal by administering a composition including a molasses extract having a relatively high abundance of hydrophobic compounds including polyphenols and a pharmaceutically acceptable carrier, excipient or diluent in an amount effective to decrease total body fat and/or minimise fat accumulation of the animal.

By "decreasing body fat", it is meant that the animal has a decrease in their amount of body fat. By "minimising fat accumulation" it is meant that the animal does not increase its amount of body fat.

The phrase "in an amount effective" is used herein to refer to an amount which is sufficient to achieve the desired outcome. For example, an amount effective to decrease body fat, minimise fat accumulation or an amount effective to reduce energy absorption. An example of an effective amount for animals is 1 to 5% of the diet, preferably 2 to 4% of the diet. Assuming that a human normally consumes 1000 g of food per day and the normal consumption of polyphenols is 1 g/day, the effective amount is likely to be in the range from 10 to 50 g/day, more preferably 20 to 40 g/day.

Without being bound by any theory, it is believed that the composition including the molasses extract having a relatively high abundance of hydrophobic compounds including polyphenols reduces energy absorption and/or alters fat metabolism. It may also influence energy expenditure. Energy expenditure is mainly a sum of internal heat produced and external work. In this context it is energy expenditure as a result of internal heat production. The internal heat produced is, in turn, mainly a sum of basal metabolic rate (BMR) and the thermic effect of food. The composition including the molasses extract having a relatively high abundance of hydrophobic compounds including polyphenols may increase the metabolism of the individual receiving the extract of the invention ie increase energy expenditure.

Accordingly, in another embodiment of the invention, there is provided a method of reducing energy absorption and/or altering fat metabolism by administering a composition including a molasses extract having a relatively high abundance of hydrophobic compounds including polyphenols and a pharmaceutically acceptable carrier, excipient or diluent in an amount effective to reduce energy absorption and/or alter fat metabolism.

In one embodiment of the invention, there is provided a method of reducing energy absorption by administering a composition including a molasses extract having a relatively high abundance of hydrophobic compounds including polyphenols and a pharmaceutically acceptable carrier, excipient or diluent in an amount effective to reduce energy absorption. More specifically the molasses extract increases the excretion of, or decreases the absorption of, carbohydrates. The invention therefore provides a method of reducing energy absorption and/or increasing energy excretion by administering a composition including a molasses extract having a relatively high abundance of hydrophobic compounds including polyphenols and a pharmaceutically acceptable carrier, excipient or diluent in an amount effective to decrease the absorption of carbohydrates and/or increase the excretion of carbohydrates.

In another embodiment of the invention, there is provided a method of altering fat metabolism by administering a composition including a molasses extract having a relatively high abundance of hydrophobic compounds including polyphenols and a pharmaceutically acceptable carrier, excipient or diluent in an amount effective to alter fat metabolism.

In one embodiment of the invention, there is provided a method of increasing basal metabolic energy expenditure in a mammal, preferably a human, by administering a composition including a molasses extract having a relatively high abundance of hydrophobic compounds including polyphenols and a pharmaceutically acceptable carrier, excipient or diluent in an amount effective to increase basal metabolic rate, thereby increasing basal metabolic energy expenditure.

In preferred embodiments, the extract represents up to 1%, 2%, 3% and 4% of the diet.

Compositions containing extracts of the invention are also envisaged to be able to improve fatigue and energy levels in healthy adults. In this embodiment of the invention, there is provided a method of alleviating or reducing the severity of fatigue by administering a composition including a molasses extract having a relatively high abundance of hydrophobic compounds including polyphenols and a pharmaceutically acceptable carrier, excipient or diluent in an amount effective to reduce energy absorption. Similarly, it is believed that administration of a composition including an extract of the invention can improve and elevate energy levels in an animal to which the composition is administered in an effective amount.

In a preferred embodiment, the extract represents at least up to 1%, 2%, 3% and 4% of the diet.

Consumption of the extracts of the invention is also thought to have other beneficial effects on individuals who are overweight. While there are a number of reasons why individuals are obese or overweight, it has been suggested that those individuals may have a deficiency in their satiation response to sucrose (Linton et al. 1972). By satiation response, or satiety, it is meant the feeling of fullness or gratification following consumption of food (ie postprandial satiety).

There is therefore provided a method of improving postprandial satiety in an individual by administering a composition including a molasses extract having a relatively high abundance of hydrophobic compounds including polyphenols in an amount effective to decrease a desire to have further food.

As an alternative to administering a composition in the methods of the invention, the individual may be administered the extract of the invention as part of a satiety inducing food.

Administration of extracts of the invention has also demonstrated effects on adipokine (gut hormone) levels, and as noted above, may therefore also have an effect on fat metabolism. One such hormone is adiponectin, a protein hormone that modulates a number of metabolic processes, including glucose regulation and fatty acid catabolism. Despite being exclusively secreted from adipose tissue into the bloodstream levels of the hormone are inversely correlated with body fat percentage in adults. Without being bound by any theory of action, it is believed that the extracts of the invention directly or indirectly lead to increased levels of adiponectin. As such, in another embodiment of the invention, there is provided a method of upregulating expression of adiponectin by administering a composition including a molasses extract having a relatively high abundance of hydrophobic compounds including polyphenols and a pharmaceutically acceptable carrier, excipient or diluent in an amount effective to upregulate expression of adiponectin.

Administration of extracts of the invention can also lead to upregulated expression of particular genes involved in regulation of energy expenditure in the liver. For example, PPAR alpha and uncoupling protein 2 (UCP2). PPAR-alpha is a regulator of lipid metabolism in the liver. Activation of PPAR-alpha promotes uptake, utilization, and catabolism of fatty acids by upregulation of genes involved in fatty acid transport and peroxisomal and mitochondrial fatty acid (β-oxidation. UCP2 is thought to have a role in fatty acid oxidation and energy expenditure through thermogenesis.

Without being bound by any theory of action, it is believed that the extracts of the invention directly or indirectly lead to increased levels of genes including PPAR-alpha and UCP2. As such, in another embodiment of the invention, there is provided a method of upregulating expression of PPAR-alpha and/or UCP2 by administering a composition including a molasses extract having a relatively high abundance of hydrophobic compounds including polyphenols and a pharmaceutically acceptable carrier, excipient or diluent in an amount effective to upregulate expression of PPAR-alpha and/or UCP2.

By "upregulating expression" it is meant increased levels of transcription of the gene, and optionally increased levels of expression of the protein product.

In a further embodiment, there is provided a method of decreasing body fat and/or minimise fat accumulation in an animal by administering a composition including a molasses extract having a relatively high abundance of hydrophobic compounds including polyphenols and a pharmaceutically acceptable carrier, excipient or diluent in an amount effective to upregulate expression of one or more of adiponectin, PPAR-alpha and UCP2.

In yet another embodiment there is provided a method of improving postprandial satiety in an individual by administering a composition including a molasses extract having a relatively high abundance of hydrophobic compounds including polyphenols and a pharmaceutically acceptable carrier, excipient or diluent in an amount effective to upregulate expression of one or more of adiponectin, PPAR-alpha and UCP2.

Administration of a composition of the invention may also be used in methods for:
- preventing and treating obesity, fatty liver, alcoholic liver, diabetes and hyperlipidemia;
- inhibiting absorption of saccharide in the body and weight increase;
- activating bifidus bacteria;
- enhancing antioxidant activity;
- improving insulin sensitivity/responsiveness;
- enhancing hypoglycaemic activity;
- enhancing tyrosine kinase inhibitory activity;
- treating pre- and post-menstrual syndromes
- treating cancer, headaches, dementia and alcoholism;
- enhancing α-amylase inhibitory activity;
- muscular strength enhancement;
- activating mitochondria.

It may also exhibit neuroprotective effects.

There is also provided use of an effective amount of a molasses extract having a relatively high abundance of hydrophobic compounds including polyphenols in the preparation of medicament for decreasing body fat, minimising fat accumulation reducing energy absorption and/or altering fat metabolism, increasing energy expenditure, improving and elevating energy levels in an animal, decreasing the absorption of carbohydrates and/or increasing the excretion of carbohydrates and improving postprandial satiety.

In a further embodiment, there is provided an effective amount of a molasses extract having a relatively high abundance of hydrophobic compounds including polyphenols for decreasing body fat, minimising fat accumulation, reducing energy absorption and/or altering fat metabolism, improving and elevating energy levels in an animal, decreasing the absorption of carbohydrates and/or increasing the excretion of carbohydrates and improving postprandial satiety.

The invention also provides a composition for decreasing body fat, minimising fat accumulation, reducing energy absorption and/or altering fat metabolism, improving and elevating energy levels in an animal, decreasing the absorption of carbohydrates and/or increasing the excretion of carbohydrates and improving postprandial satiety, the composition comprising as an active ingredient a molasses extract having a relatively high abundance of hydrophobic compounds including polyphenols.

iv) Use of the Molasses Extract as an Ingredient

The molasses extract of the invention having a relatively high abundance of hydrophobic compounds including polyphenols may also be administered to an animal as an ingredient in a food or beverage. The extracts are preferably produced by the method of the invention.

The therapeutic compositions of the invention may also be incorporated into foods, including pet foods.

The extracts of the present invention may be incorporated into food products and beverages. The extracts may be impregnated, mixed, emulsified, sprayed or coated onto carriers such as cellulose, methylcellulose, dextrose, cyclodextrose, cyclodextrin, maltitol, fibre and fibre containing bioactives to improve delivery. Delivery may also be enhanced with a range of surfactants, lipids, complexes, solvents and co-solvent pharmaceutical delivery systems known in the pharmaceutical art to improve bioavailability, absorption and efficacy.

As used herein, the term "food" or "food product" includes any edible product for human or non-human consumption, such as but not limited to confectioneries, supplements, snacks (sweet and savoury), cocoa-containing foods, flavours, beverages, dietary supplements and formulations including supplements used in animal health and nutrition. Additional ingredients desired in the resulting food product may be added at any point in the process. In one embodiment of the invention, the extracts are in the form of syrups that can be used as substitutes for regular glucose and high fructose corn syrups from wheat, corn, agave, stevia etc., as a lower Glycemic Index (GI) option.

The extracts of the present invention may be incorporated into foods, beverages and nutraceuticals, including, without limitation, the following:
- Dairy Products—such as cheeses, butter, milk and other milk or dairy containing beverages, spreads and dairy mixes, ice cream and yoghurt;
- Fat-Based Products—such as margarines, spreads, mayonnaise, shortenings, cooking and frying oils and dressings;
- Cereal-Based Products—comprising grains (for example, bread and pastas) whether these goods are cooked, baked or otherwise processed;
- Confectioneries—such as chocolate, candies, chewing gum, desserts, non-dairy toppings, sorbets, icings and other fillings;
- Sports nutrition products including powders, pre-mixes, juices, energy bars, isotonic drinks and gelatine, starch based or pectin jellies;
- Beverages—whether hot or cold (coffee, tea, cocoa, cereal, chicory and other plant extract based beverages), alcoholic beverages, carbonated, non-carbonated and lightly carbonated beverages including colas and other soft drinks, powdered soft drinks, fruit and vegetable juice drinks, dietary supplement, breakfast beverages, instant pre-mixes and meal replacement drinks; sport drinks, energy drinks, flavoured water drinks;
- animal feeds including pet foods for companion animals such as dogs, cats and horses;
- Miscellaneous Products—including eggs and egg products, processed foods such as soups, pre-prepared pastas.

Similarly, food grade ingredients such as soluble fiber (e.g. oligofructosaccharide), insoluble fiber (e.g. sugar cane fiber, oat bran), flour, starch, modified starch, gelatine, or other food, pharmaceutical or cosmetic ingredients impregnated with or containing the extract according to the invention, can produce a unique food ingredient with enhanced levels of hydrophobic compounds including polyphenols.

The present invention includes food products comprising an extract according to the invention alone as the active ingredient or in combination with other active ingredients.

In one embodiment, there is provided a breakfast beverage including a molasses extract having a relatively high abundance of hydrophobic compounds including polyphenols.

In another embodiment, there is provided a carbonated or low carbonated beverage including a molasses extract having a relatively high abundance of hydrophobic compounds including polyphenols. Carbonated and low carbonated beverages are also known in the art as soft drinks.

In yet another embodiment, there is provided a satiety inducing food including a molasses extract having a relatively high abundance of hydrophobic compounds including polyphenols.

In yet another embodiment, there is provided a pet food including a molasses extract having a relatively high abundance of hydrophobic compounds including polyphenols, wherein the pet food is preferably for companion animals including cats, dogs and horses.

v) Use of the Molasses Extract to Reduce GI

The molasses extract of the invention having a relatively high abundance of hydrophobic compounds including polyphenols may be added other substances or ingredients to reduce the GI of that substance. By "reduce the GI" it is meant that the GI of the substance to which the extract is added is lowered compared to the naturally occurring GI of the substance. It does not have to make the substance itself low GI (ie GI<55), although it may in fact do so depending on the substance.

In particular, the molasses extract having a relatively high abundance of hydrophobic compounds including polyphenols may be used to reduce the GI of mono- and disaccharides.

Monosaccharides are the most basic units of biologically important carbohydrates. They are the simplest form of sugar and are usually colorless, water-soluble, crystalline solids. Examples of monosaccharides include glucose (dextrose), fructose (levulose), galactose, xylose, ribose, mannose, rhamnose and xylopyranose.

For example, glucose (dextrose) was described above as being a suitable carrier for the extract for use in foods. In addition to that, impregnating, mixing, emulsifying, spraying or coating the molasses extract having a relatively high abundance of hydrophobic compounds including polyphenols on to glucose can reduce the natural GI of glucose. In turn, food prepared using glucose with a reduced GI also has a reduced GI.

There is therefore provided a monosaccharide having a GI that is reduced from its naturally occurring GI, comprising a molasses extract having a relatively high abundance of hydrophobic compounds including polyphenols added to the monosaccharide. There is also provided a monosaccharide having a GI that is reduced from its naturally occurring GI, consisting essentially of a molasses extract having a relatively high abundance of hydrophobic compounds including polyphenols added to the monosaccharide. By "consisting essentially of" it is meant that there is only the extract and the monosaccharide. The presence of any other ingredients would only be in trace amounts, and would not be present in sufficient amounts to have any effect on, or to counteract the GI lowering characteristics of the molasses extract on the monosaccharide.

There is also provided a method for reducing the GI of a monosaccharide, comprising the addition of a molasses extract having a relatively high abundance of hydrophobic compounds including polyphenols to the monosaccharide. Preferably the monosaccharide is glucose. The molasses extract can be impregnated, mixed, emulsified, sprayed or coated on to the monosaccharide.

There is also provided a method of reducing the GI of a food by replacing a monosaccharide present in or used in the food with a monosaccharide to which a molasses extract having a relatively high abundance of hydrophobic compounds including polyphenols has been added, and wherein the monosaccharide to which the extract is added has a reduced GI compared to the monosaccharide being replaced.

Addition of a molasses extract having a relatively high abundance of hydrophobic compounds including polyphenols to disaccharides can also reduce the GI of the disaccharide. Disaccharides are formed when two monosaccharides undergo a condensation reaction. Like monosaccharides, disaccharides also dissolve in water, taste sweet and are called sugars. Table 1 provides list of disaccharides, including their monomeric components. There is therefore provided a disaccharide having a GI that is reduced from its naturally occurring GI, comprising a molasses extract having a relatively high abundance of hydrophobic compounds including polyphenols added to the disaccharide. In another embodiment, there is provided a disaccharide having a GI that is reduced from its naturally occurring GI, consisting essentially of a molasses extract having a relatively high abundance of hydrophobic compounds including polyphenols added to the monosaccharide. There is further provided with a method for reducing the GI of a disaccharide, comprising the addition of a molasses extract having a relatively high abundance of hydrophobic compounds including polyphenols to the disaccharide. Preferably the disaccharide is sucrose. The molasses extract may be impregnated, mixed, emulsified, sprayed or coated on to the disaccharide.

There is also provided a method of reducing the GI of a food by replacing a disaccharide present in or used in the food with a disaccharide to which a molasses extract having a relatively high abundance of hydrophobic compounds including polyphenols has been added, and wherein the disaccharide to which the extract is added has a reduced GI compared to the disaccharide being replaced. Preferably the disaccharide is sucrose.

TABLE 4

| Disaccharide | Units | Bond |
|---|---|---|
| Sucrose | One glucose monomer and one fructose monomer | $\alpha(1\rightarrow 2)\beta$ |
| Lactulose | One galactose monomer and one fructose monomer | $\beta(1\rightarrow 4)$ |
| Lactose | One galactose monomer and one glucose monomer | $\beta(1\rightarrow 4)$ |
| Maltose | two glucose monomers | $\alpha(1\rightarrow 4)$ |
| Trehalose | two glucose monomers | $\alpha(1\rightarrow 1)\alpha$ |
| Cellobiose | two glucose monomers | $\beta(1\rightarrow 4)$ |
| Kojibiose | two glucose monomers | $\alpha(1\rightarrow 2)$ |
| Nigerose | two glucose monomers | $\alpha(1\rightarrow 3)$ |
| Isomaltose | two glucose monomers | $\alpha(1\rightarrow 6)$ |
| β,β-Trehalose | two glucose monomers | $\beta(1\rightarrow 1)\beta$ |
| α,β-Trehalose | two glucose monomers | $\alpha(1\rightarrow 1)\beta$ |
| Sophorose | two glucose monomers | $\beta(1\rightarrow 2)$ |
| Laminaribiose | two glucose monomers | $\beta(1\rightarrow 3)$ |
| Gentiobiose | two glucose monomers | $\beta(1\rightarrow 6)$ |
| Turanose | a glucose monomer and a fructose monomer | $\alpha(1\rightarrow 3)$ |
| Maltulose | a glucose monomer and a fructose monomer | $\alpha(1\rightarrow 4)$ |
| Palatinose | a glucose monomer and a fructose monomer | $\alpha(1\rightarrow 6)$ |
| Gentiobiulose | a glucose monomer and a fructose monomer | $\beta(1\rightarrow 6)$ |
| Mannobiose | two mannose monomers | $\alpha(1\rightarrow 2)$, $\alpha(1\rightarrow 3)$, $\alpha(1\rightarrow 4)$, or $\alpha(1\rightarrow 6)$ |
| Melibiose | a galactose monomer and a glucose monomer | $\alpha(1\rightarrow 6)$ |
| Melibiulose | a galactose monomer and a fructose monomer | $\alpha(1\rightarrow 6)$ |
| Rutinose | a rhamnose monomer and a glucose monomer | $\alpha(1\rightarrow 6)$ |
| Rutinulose | a rhamnose monomer and a fructose monomer | $\beta(1\rightarrow 6)$ |
| Xylobiose | two xylopyranose monomers | $\beta(1\rightarrow 4)$ |

As outlined above, the molasses extracts of the invention can be used as substitutes for regular glucose and high fructose corn syrups from wheat, corn, agave, stevia etc., as a lower Glycemic Index (GI) option. Alternatively, in another embodiment of the invention, the molasses extracts having a relatively high abundance of hydrophobic compounds including polyphenols can be used to reduce the GI of such sweeteners. Corn syrup (also known as glucose syrup) is a food syrup made from the starch of maize. It contains varying amounts of glucose, maltose and higher oligosaccharides. Enzymatic processing of corn syrup converts glucose to fructose, creating high fructose corn syrup (HFCS). HFCS is sweeter and more soluble than corn syrup, and in the United States in particular, is a cheaper alternative to sucrose. Accordingly, HFCS has replaced sucrose in the food industry, and is commonly used in many processed foods and beverages.

There is therefore provided a corn syrup, particularly high fructose corn syrup (HFCS), having a GI that is reduced from its naturally occurring GI, consisting of a molasses extract having a relatively high abundance of hydrophobic compounds including polyphenols added to the HFCS, together with a method for reducing the GI of HFCS, comprising the addition of a molasses extract having a relatively high abundance of hydrophobic compounds including polyphenols to HFCS. Preferably the molasses extract is impregnated, mixed, emulsified, sprayed or coated on to the HFCS.

There is also provided a method of reducing the GI of a food by replacing HFCS used in the food with HFCS to which a molasses extract having a relatively high abundance of hydrophobic compounds including polyphenols has been added, and wherein the HFCS to which the extract is added has a reduced GI compared to the HFCS being replaced.

It will be understood that the invention disclosed and defined in this specification extends to all alternative combinations of two or more of the individual features mentioned or evident from the text or drawings. All of these different combinations constitute various alternative aspects of the invention.

The invention is now described with reference to the following non-limiting examples.

EXAMPLES

1. Molasses Extract Production Method

An extract from molasses was prepared by the method of the invention but subject to a number of variables as per the following:

it with 40% ethanol. The lower concentration ethanol solution is also advantageous from a cost and safety perspective.

2. Characterisation of the Molasses Extract i) Polyphenols

To further characterize the types of polyphenols found in the molasses extract of the invention, a combined HPLC and tandem mass spectrometry procedure was performed.

Sample Extraction and Preparation: 1.5 g of extract was placed into 10 mL of 80% methanol (150 mg/mL), and extracted overnight at 4° C. After extraction the sample was centrifuged at 18,000×g for 10 minutes to pellet particulate matter. 1 mL of the centrifuged material was placed into a glass tube, and the sample was dried completely using air. Once dried the sample was resuspended in 500 µL of 0.1% formic acid (concentration ~300 mg extract), for HPLC analysis.

HPLC Analysis: An Agilent 1100 HPLC with Diode Array Detector was used for all analyses. The HPLC Column used was a Phenomenex Luna 5 u C18(2) 100 angstrom 250×4.6 mm, with Widepore C18 4×2.0 mm guard cartridge. All solvents were of HPLC grade, and doubly distilled water was used. Solvent A: 2% acetonitrile/0.1% formic acid Solvent B: 90% acetonitrile/0.1% formic acid.

Column washed with 100% Solvent B, and equilibrated in 100% Solvent A prior to the start of the run. 20 µL of the resuspended sample (~15 mg extract) was injected onto the column. For the gradient and fractionation of the extract, the column was equilibrated at 0% Solvent B followed by 0-30% Solvent B (2-27% acetonitrile) over 90 minutes; then 30-100% Solvent B (27-90% acetonitrile) over 1 minute; then hold 100% Solvent B (90% acetonitrile) over 10 minutes; then 100-0% Solvent B (90-2% acetonitrile) over 1 minute; then hold 0% Solvent B (2% acetonitrile) for 8 minutes. Fractions were collected in 5 minute intervals over the course of the HPLC run (signals monitored: 262 nm, 4 nm bandwidth—reference 308 nm, 40 nm bandwidth), air dried, and subjected to mass spectrometric (MS) analysis.

MS analysis identified a number of peaks identified as being the following:

TABLE 5

| Method A | Step | Method B |
| --- | --- | --- |
| Diluted to 20% molasses with water | Molasses preparation | Diluted to 20% molasses with water |
| Centrifugation | Molasses clarification | Filtration through a 0.1 µM stainless steel filter |
| Sample applied to column for at least about 60 minutes, at ambient temperature | Hydrophobic adsorbent column purification | Sample cycled 3 times over column at a flow rate of 4 L/min |
| Purified water | Wash | Purified water |
| 70% Ethanol | Elution | 40% Ethanol |

The total phenolics were measured in an extract derived from method A and compared to method B. The amount of polyphenols in the molasses extract were determined as described in Kim, Dae-Ok, et al (2003) Antioxidant capacity of phenolic phytochemicals from various cultivars of plums. *Food Chemistry*, 81, 321-26.

| Method A batch | 185.4 mg CE/g (18540 mg CE/100 g) |
| --- | --- |
| Method B batch | 193.3 mg CE/g (19330 mg CE/100 g) |

Method B was found to have 5% more phenolic content, indicating an advantage to filtering the extract, and eluting free form polyphenols—apigenin, catechin, catechin gallate, epicatechin, kaempherol, diosmin, luteolin, quercetin, tricin, myricetin and diosmetin polyphenol glycosides—diosmin, tricin-7-O-neohesperidoside, orientin, vitexin, luteolin-8-C-(rhamnosylglucoside), schaftoside, isoschaftoside, and rutin phenolic acids—caffeic acid, chlorogenic acid, p-coumaric acid, ferulic acid, gallic acid, syringic acid and vanillic acid.

Quantification of Selected Polyphenols

The levels of a number of the polyphenols was determined in aqueous acidic and basic fractions of the molasses extract following ethyl acetate extraction. Ethyl acetate extraction was carried out on both acidified and basified aqueous solutions of the samples to ensure that as many compounds as possible would be extracted from the samples. An aliquot of each sample (~200 mg) was dissolved in water (10 mL) that had been acidified (pH 1.6) or basified (pH 9.6). Methyl-4-formyl benzoate (7.4 µg) was added to each solution as an internal standard (ISTD). The mixtures were then extracted with ethyl acetate (2×10 mL), the solvent was evaporated under vacuum (40° C.) and the mixtures were reconstituted in aqueous formic acid (0.1%, 5 mL) before subjected to HPLC and LC/MS analysis.

TABLE 6

|  | Amount in sample (mg/Kg) | |
| --- | --- | --- |
|  | Extract - Acid | Extract - Basic |
| Apigenin | 34.8 | not detected |
| Catechin | not detected | 175.2 |
| Epicatechin | 168.8 | 207.4 |
| Luteolin | 18.6 | 41.3 |
| Quercetin | 91.3 | 137.1 |
| Rutin | 59.3 | 59.3 |
| Diosmin | 303.6 | 114.3 |
| Caffeic Acid | 168.8 | 207.4 |
| Chlorogenic Acid | 368.2 | 123.1 |
| p-Coumaric Acid | 1170.9 | 1253.8 |
| Ferulic Acid | 738.8 | 724.1 |
| Syringic Acid | 433.5 | 472.6 |
| Vanillic Acid | 2.13 | not detected | ii) Trace Elements

Trace elements were determined by inductively coupled plasma-mass spectrometry (ICP-MS) and inductively coupled atomic emission spectrometry (ICP-OES). 10 g of molasses extract was used for the analysis. The sample was homogenised and a sub-sample (0.2-0.5 g) digested with re-distilled nitric acid on a DigiPrep block for one hour until vigorous reaction was complete. Samples were then transferred to a Milestone microwave to be further digested. After making up to appropriate volume with Milli-Q (high purity) water, the digest was analysed for trace elements using ICP-MS and/or ICP-OES. The results were as follows:

TABLE 7

| Trace Elements | Concentration |
| --- | --- |
| Calcium | 8800 mg/kg |
| Iron | 860 mg/kg |
| Magnesium | 2000 mg/kg |
| Manganese | 65 mg/kg |
| Potassium | 190 mg/kg |
| Sodium | 30 mg/100 g | iii) Sugar Determination

About 15 grams of molasses extract was used for the analysis. The sample was homogenised and a sub sample was accurately weighed. Sugars were extracted with 25 mL water at 60° C. for 30 minutes. The extract was clarified with 25 ml acetonitrile and filtered through a 0.45 um filter into a 2 mL vial, suitable for HPLC. For the determination of common sugars, the filtered solution was analysed by HPLC using amino column with an acetonitrile/water mobile phase containing salt and refractive index detection. Quantitation was made against a standard solution containing known amounts of fructose, glucose, sucrose, maltose and lactose. For the determination of low level sugars, the filtered solution was analysed by HPLC using carbohydrate ES column with an acetonitrile/water mobile phase and evaporative light scattering detector (ELSD). Quantitation was made against a standard solution containing known amounts of fructose, glucose, sucrose, maltose and lactose. Result calculation was performed by the HPLC software and a report generated. The molasses extract contained the following sugars as summarized in the table below.

TABLE 8

| Sugars | Concentration |
| --- | --- |
| Fructose | <0.2 g/100 g |
| Glucose | <0.2 g/100 g |
| Sucrose | 0.3 g/100 g |
| Maltose | <0.2 g/100 g |
| Lactose | <0.2 g/100 g |
| Maltotriose | <0.2 g/100 g |
| Total Sugars | <1 g/100 g | iv) Protein

The total nitrogen was determined by the Kjeldahl method, as would be known to the person skilled in the art, and the protein amount estimated from that by multiplying the total nitrogen by a factor (6.25). The molasses extract was homogenised and a sub sample (approx. 2 g) was accurately weighed into a Kjeldahl digestion tube. A digestion aid of potassium sulphate and a catalyst, copper sulphate was added to the sample, followed by 20 mL of concentrated sulphuric acid. The tube was slowly heated to 400° C. and the temperature maintained until the mixture in the tube was clear. The clear solution was digested for 1 hour and the tube allowed to cool.

Once the tube had cooled 50 mL of distilled water was added. The tube was placed in a Kjeltec distillation unit and the mixture was steam distilled into a beaker containing 50 mL of saturated boric acid solution. The distilled solution was titrated with standardised 0.1N sulphuric acid solution using a mixed indicator of bromocresol green and methyl red. Calculations: The following equation was used to calculate total nitrogen: Total N (g/100 g)=0.14*(titre-blank)/sample mass or volume. For protein estimation the total N was multiplied by 6.25.

From this method, the protein content of the molasses extract was calculated to be 12.6 g/100 g.

To identify the protein components of the molasses extract, a sample of the extract was run on an SDS-PAGE gel for visualization and mass spectrometric analysis after in-gel trypsin digestion. 20 mg of molasses extract was dissolved in 1 mL of 1×XT Sample Buffer. The sample was centrifuged at 16,000×g for 5 minutes to pellet any particulates.

Two SDS-PAGE gels were run, one for in-gel trypsin digestion and one for visible protein analysis. 12% Criterion Bis-Tris XT gels were used, with their corresponding buffers. 30 µg of protein were run four times on each gel.

In-Gel Digestion: Samples were loaded onto the gel in a total volume of 26.25 µL (containing the 30 µg of protein). The gel was run at 75 V for 5 minutes, and then 120 V for 10 minutes, which placed the proteins 1.5 cm into the gel. The gel was fixed in 30% methanol/10% acetic acid for 10 minutes, and washed twice with ddH$_2$O for five minutes each. After washing, each of the four gel bands were cut to just below the dye front, diced, and placed into 1.5 mL micro-centrifuge tubes to which 50 mM ammonium bicarbonate/50% acetonitrile was added to destain the samples.

After de-staining the samples were reduced with 30 mM dithiothreitol, and alkylated with 55 mM iodoacetamide. After alkylation the gel bands were dehydrated, and then overlaid with a 1:20 ratio of trypsin to protein, and covered in 100 mM ammonium bicarbonate to increase the sample pH to between 7-8. The bands were then allowed to digest overnight. Peptides were extracted using 50% acetonitrile/5% formic acid. After extraction the liquid containing peptides was dried, resuspended in 0.1% formic acid, and desalted using a ZipTip procedure. De salted samples were again dried and resuspended in 0.1% formic acid for mass spectrometric analysis.

Tandem mass spectra were obtained and some peptide sequences were deduced by manual inspection. These peptide sequences were unique and not found in any known genomic databases. In the absence of the sugarcane genome sequence it was not possible to confirm whether these peptide sequences are from sugarcane.

v) Carbohydrate Analysis

To get an empirical and more quantitative determination of the carbohydrate content of the molasses extract the glycosyl composition of the extract was analysed. Glycosyl composition analysis was performed by combined gas chromatography/mass spectrometry (GC/MS) of the per-O-trimethylsilyl (TMS) derivatives of the monosaccharide methyl glycosides produced from a sample of the molasses extract by acidic methanolysis.

20 μg of inositol was added to 300 μg of molasses extract. Methyl glycosides were then prepared from the dry sample by methanolysis in 1M HCl in methanol at 80° C. (17 hours), followed by re-N-acetylation with pyridine and acetic anhydride in methanol (for detection of amino sugars). The sample was then per-O-trimethylsilylated by treatment with Tri-Sil (Pierce) at 80° C. (0.5 hours). These procedures were carried out as previously described in Merkle and Poppe (1994) Methods Enzymol. 230: 1-15; York, et al. (1985) Methods Enzymol. 118:3-40. GC/MS analysis of the TMS methyl glycosides was performed on an Agilent 6890N GC interfaced to a 5975B MSD, using a Supelco EC-1 fused silica capillary column (30 m×0.25 mm ID).

TABLE 9

| Glycosyl residue | Mass (ug) | Mol %[1] |
|---|---|---|
| Arabinose (Ara) | 0.6 | 0.6 |
| Rhamnose (Rha) | 0.8 | 0.8 |
| Fucose (Fuc) | n.d. | — |
| Xylose (Xyl) | 0.9 | 0.9 |
| Glucuronic Acid (GlcA) | n.d. | — |
| Galacturonic acid (GalA) | n.d. | — |
| Mannose (Man) | 0.2 | 0.1 |
| Galactose (Gal) | 0.1 | 0.1 |
| Glucose (Glc) | 112.2 | 97.5 |
| N-Acetyl Galactosamine (GalNAc) | n.d. | — |
| N-Acetyl Glucosamine (GlcNAc) | n.d. | — |
| N-Acetyl Mannosamine (ManNAc) | n.d. | — |
| Total | 114.7 | |

[1]Values are expressed as mole percent of total carbohydrate. The total percentage may not add to exactly 100% due to rounding.
"n.d" is not detectable.

As can be seen from the results in the table above, the carbohydrate content of the molasses extract is predominantly composed of glucose residues with a small amount of other monosaccharides also detected.

vi) Moisture Content

About 10 g of molasses extract was homogenised for moisture determination by either using sand and vacuum drying (Sand method) or no sand and conventional drying (no sand method).

Sand method: A moisture dish with sand, lid and glass rod was oven-dried at 102° C. and cooled before all dried components were weighed together to the nearest 0.1 mg. 2 to 5 g of sample was weighed, to nearest 0.1 mg, into the moisture dish. Water was added to the dish to aid mixing of the sample and sand. The moisture dish was placed on a steam bath until visible dryness of the sand/sample mix was achieved. The dish and components were placed in a vacuum oven and dried under vacuum (approx. 5 kpa) at between 70 and 100° C. depending on the sugar content of the sample. Drying time was a minimum of 4 hours depending on the sample matrix. After the required initial drying period the moisture dish and components were removed, cooled, re-weighed and returned for a further 1 hour drying. The weighing and drying process was repeated until constant weight is obtained.

No sand method: A moisture dish and lid was placed in the oven at 102° C. dried and cooled. The dried components were weighed together to the nearest 0.1 mg. A portion of sample (2 to 5 g) was weighed, to nearest 0.1 mg, into the dish. The sample in the dish was then placed in a conventional oven at 102° C. for a minimum of 4 hours depending on the sample matrix. The dish and lid were then removed, cooled, re-weighed and returned for a further 1 hour drying. The weighing and drying process was repeated until a constant weight was obtained.

To determine moisture content in both methods, the mass of the dish (plus components or lid depending on the method) was subtracted from the mass of dried sample and dish (plus components or lid), then divided by the sample mass obtained. The final result was then multiplied by 100 to obtain a result as % moisture or g/100 g. Both methods determined the moisture content of the molasses extract to be 5.9 g/100 g of extract.

vii) Ash Analysis

Ash content was determined by weighing 10 g of sample into a prepared weighed dish, beaker or crucible. The sample was dispersed on bottom of container, and excess moisture removed in a water bath. The container was then transferred to a muffle furnace and slowly heated to 525° C.±25° C. until all organic matter was destroyed. Dissolving salts in water enhanced destruction of occluded carbon particles. The remaining ash product was weighed and was found to be present as 3.1 g per 100 g of extract.

vii) Fat and Fatty Acid Analysis

Fat content was determined by the Mojonnier extraction method (Mills B L et al (1983) J Assoc Off Anal Chem 66(4):1048-50)). About 10 g of molasses extract was homogenised and a sub sample (approx. 2 g) was accurately weighed into a beaker. 10 mL of approx. 10% hydrochloric acid was added and the mixture was heated at 80° C. until hydrolysis was complete (approx. 0.5 hours). The mixture was cooled and transferred quantitatively to a Mojonnier tube. 10 mL of ethanol was added and the fat was extracted by shaking for 1 minute with 25 ml of diethyl ether and a further minute with each of 25 ml of petroleum ether and 50 ml petroleum and diethyl ether mix (The petroleum and diethyl ether mix extract was conducted twice). After each solvent addition, and subsequent shaking, the organic layer was decanted from the Mojonnier tube into a pre-weighed glass dish. Once all extractions were complete the organic extract in the glass dish was evaporated. The dish was then dried in an oven at 102° C. until constant weight was achieved.

Calculation: % Fat=[(Weight of dish−Weight of dish)/Weight of sample]×100. Using this calculation, no detectable fat was found in the molasses extract of the invention, wherein "no detectable fat" was<0.2 g of fat/100 g of extract.

In addition to analysing the fat content of the molasses extract, fatty acid composition was also investigated, based on 10 g of molasses extract. The sample was homogenised and a sub sample taken (about 1 g). Fat was extracted from the sample using either Chloroform/Methanol or Petroleum ether/iso-propyl alcohol. The extract was evaporated under nitrogen. A minimum extracted mass of 0.2 g fat was required. The extracted fat was esterified using a methanolic sodium methoxide solution and treatment with sulphuric acid in methanol. The solution was neutralised and re-extracted using n-hexane. The hexane layer was removed, dried using anhydrous sodium sulphate and made to volume, with hexane.

The relative proportion of each fatty acid methyl ester in the prepared sample was determined using gas chromatography with flame ionisation detection. Identification of the individual fatty acids was made by retention time against a standard of known fatty acid methyl esters including both cis and trans isomers. The amount of Conjugated Linoleic Acid (CLA) can be also determined from the FAME's chromatogram. Instrument software was used to provide the calculation of proportional methyl ester concentrations.

As can be seen from the table below, no detectable fatty acids were present in the molasses extract (reported as g of fat/100 g of extract):

TABLE 10

| Saturated fat | <0.1 g/100 g |
| Mono trans fat | <0.1 g/100 g |
| Mono-unsaturated fat | <0.1 g/100 g |
| Omega 3 fats | <0.1 g/100 g |
| Omega 6 fats | <0.1 g/100 g |
| Poly trans fats | <0.1 g/100 g |
| Poly-unsaturated fat | <0.1 g/100 g |
| Trans fats | <0.1 g/100 g | viii) Antioxidant Activity

The ORAC value, indicative of the amount of antioxidant scavenging activity of the molasses extract of the invention was calculated by the method described in Cao G, Alessio H, Cutler R (1993). "Oxygen-radical absorbance capacity assay for antioxidants". *Free Radic Biol Med* 14 (3): 303-11. The ORAC Vitamin E equivalents of the extract were calculated to be 383070 µmol TE/100 g.

3. Impact of Consumption of the Molasses Extract on Weight

In this example, an extract of the invention (prepared by Method A referred to above in Example 1) was mixed into a high-fat, high-carbohydrate rodent diet to determine if their intake assists in preventing the development of obesity, and that the extract does so by increasing energy excretion and/or by influencing mechanisms involved in fat and sugar oxidation and insulin sensitivity. The results described below were also confirmed in a cat model (data not shown), which showed both decreased body fat and minimisation of fat accumulation.

Methods

45 C57Bl/6J male mice were maintained on a high fat-high carbohydrate diet containing 2% or 4% of an extract of the invention or a control additive. The animals were fed the diets for 12 weeks from six weeks of age. During this 12 week period, the mice were monitored daily, their food and water intake and body weight were measured three times per week, and faeces were collected to determine energy content.

While the animals were maintained on the experimental diets the following procedures were performed:
Week 1—indirect calorimetry
Week 8—faecal energy excretion
Week 10—glucose tolerance test
Week 12—body composition (DEXA) was analysed and while still under anaesthetic the animals were killed by terminal bleeding (via cardiac puncture) and blood and tissue (brain, adipose tissue, liver and muscle) samples were collected.

1. LabMaster—calorimetry and activity

In their first week on the experimental diets, mice were assessed in the LabMaster System. Prior to commencement of calorimetry measurement, the LabMaster system was calibrated with standard gases, drinkers and food containers were filled and bedding was placed into the cages. Mice were placed into the LabMaster cages individually and allowed to acclimate for 24 hours. Following this, the system recorded data for the animal for a further 24 hours before the mouse was returned to its home cage.

2. Faecal energy excretion

Faeces samples (from week eight) were collected from each of the mice, and were placed, in individual foil containers in an oven at 83° C. for 48 hours. Following this, each sample was ground into a powder using a homogeniser and was pressed into a pellet (~0.6 g) using a pellet press (Model 2811, Parr Instruments, Moline Ill.). The pellet was placed into a crucible atop a support stand, and a 10 cm length of fuse wire was fastened between the two electrodes. The sample was then arranged inside a bomb (Model 1108 oxygen bomb, Parr Instruments, Moline Ill.), with 1 ml of water, which was flushed of atmospheric nitrogen and refilled with oxygen. Prior to commencement of the bombing procedure, the calorimeter was calibrated using a benzoic acid standard in order to verify the chemistry of the combustion method and the precision of the energy amendments involved in the analysis of the results. The calorimeter (Model 1261 Parr Instruments, Moline, Ill.) was filled with two liters of deionised water, and the bomb was gently lowered inside, ensuring that prior to submersion the ignition wires were inserted into the two terminal sockets on the bomb head. The oxygen was then combusted, and the pellet was ignited by the passage of current through the fuse wire. The temperature measurement took place directly in the bomb and caloric value was calculated from the heat released during the combustion process. This energy value of the faeces was calculated in MJ/kg.

3. Faecal Lipid, Carbon and Nitrogen Analysis

Faecal lipid content was determined by mixing 100 mg of ground faeces with 4 ml of chloroform/methanol (2:1) and incubating at 60° C. for 30 minutes. The samples were passed through a Whatman No. 1 filter (Sigma-Aldrich Pty. Ltd., Castle Hill, NSW, Australia) into pre-weighed weighing boats and placed under a fume hood to allow solvent evaporation. After the weight stabilised, the difference in weight between empty weighing boats and weighing boats containing the dried material was the faecal lipid amount, which was expressed as a percentage of the weight of the starting faecal sample.

Carbon (C) and Nitrogen (N) analysis was carried out from dried homogenised faeces powder. The faecal C and N contents were analysed using the vario EL III CHNOS elemental analyser (Elementar Analysensysteme GmbH, DonaustraBe, Germany) Approximately 20 mg homogenized samples were packed in tin foil and weighed. The samples were combusted and $CO_2$ was retarded in an adsorption trap. $N_2$ was then measured directly in the thermal conductivity detector. After the N-measurement, the $CO_2$ was thermally desorbed and measured.

4. Glucose Tolerance Test

To assess glucose tolerance, mice were fasted overnight (with ad lib water). The mouse was placed into a restraint tube, and a basal fasting blood glucose level was obtained by removing the tip of the tail with a razor blade (approx. 1 mm) and withdrawing ~5 µl of whole blood into a heparin-containing microcuvette (Hemocue, Medipac Scientific NSW). This was then inserted into the glucose monitor (Hemocue 201+, Medipac Scientific, NSW) and the fasting glucose concentration was recorded.

Subsequently, the mice were injected intraperitoneally with glucose solution (1 g/kg body weight) using a 0.5 ml diabetic syringe. Animals were then returned to the home cage and additional blood samples were obtained from the same tail cut at 30, 60 and 120 minutes post glucose loading.

5. Body Composition Analysis by Dual Energy X-Ray Absorptiometry (DEXA)

Following 12 weeks on the experimental diets, in vivo body composition of the mice was assessed using Dual energy x-ray absorptiometry (DEXA) (Norland pDEXA Sabre, Norland Medical Systems, White Plains, N.Y.).

Prior to scanning, the DEXA machine was calibrated using quality assurance and quality control standards of known mass supplied by the manufacturer. The mice were anaesthetised by means of an injection into the intraperitoneal cavity (ketamine 61 mg/kg and xylazine 9 mg/kg.), and were placed in the prone position on the DEXA scanning platform, with the tail secured by tape.

The animals were scanned and results were obtained for fat and fat-free mass, as well as bone mineral content and density. Once scanning was complete, the animals were killed by terminal bleeding (via cardiac puncture) whilst still anaesthetised.

6. Enzyme-linked Immunosorbent Assays (ELISA)

The concentration of leptin and adiponectin present in the mice plasma was quantified by Enzyme-linked immunosorbent assay (ELISA) (LINCO, Missouri USA). The ELISA microtiter plate wells came with antibodies bound to the surface, and the antigen-containing sample was added to this. The plate was then washed to remove the unbound proteins. The antigen-specific antibodies were added, followed by a substrate designed to create an oxidative reaction with the enzyme labelled antibody and generate a colour formation proportionate to the amount of antigen present in the sample. Stop solution was then added to acidify the sample and cease the reaction. The enzyme activity was analysed in a spectrophotometer. The degree of absorbency detected by the spectrophotometer is directly proportionate to the amount of antigen present, the concentration was then elucidated from a reference curve produced within the same assay from reference standards of known concentration.

7. In Vivo Visualization of Distribution of Adipose Tissue by Magnetic Resonance Imaging (MRI)

After 14 weeks (2 weeks after cessation of diet supplementation), the body fat deposition of 6 mice (n=2 per group) was assessed with magnetic resonance imaging (MRI). The animals were sacrificed using $CO_2$ gas, positioned prone on cardboard with their limbs splayed, placed on ice, and transported to the Howard Florey Institute at Melbourne University.

Regional body fat distribution was visualized by magnetic resonance imaging (MRI). Images were acquired on a Bruker BIOSPEC 47/30 MRI scanner, equipped with a horizontal 4.7 Telsa Oxford magnet. Proton density weighted axial images with the following parameters: number of slices, 20; slice thickness, 1 mm; field of view (FOV), 6 cm; matrix size, 256×256; repetition time (TR), 815 ms; echo time (TE), 17.9 ms were acquired.

8. Analysis of mRNA Expression

Total RNA was extracted from ~100 mg of adipose or liver tissue using Tri-reagent (PE Applied Biosystems, CA, USA). Nanodrop 1000 (Thermo Fisher Scientific Inc, MA, USA) was used to determine the purity of RNA and the ratio (A260/A280) values were close to 2.0. High capacity cDNA reverse transcription kit (PE Applied Biosystems, CA, USA) was used to synthesise cDNA from 0.5 µg of RNA from the tissue in a total of 20 µL of reaction volume. Reverse transcription was performed by incubating the samples at 25° C. for 10 min, 37° C. for 120 min, 85° C. for 5 sec followed by 4° C. for 30 sec. RT-PCR amplification was performed using 1 µl of cDNA diluted at 1:10 using gene specific primer sets (GeneWorks Pty Ltd, SA, Australia). The oligonucleotide sequences of the forward (sense) and reverse (antisense) primers used for amplification were as in Table 1. Each primer set was used at a concentration of 3.75 µM in a final volume of 25 µL using the Brilliant® II SYBR® Green QRT-PCR Master Mix Kit, 1-Step (Agilent Technologies, Inc., CA, USA). Real-time PCR was performed using the MX3000P qPCR machine (Agilent Technologies, Inc., CA, USA) where target expression was normalised to the amount of endogenous control (beta actin) relative to CON value, given by ΔΔCT method.

TABLE 11

| Gene | Forward Primer (5'-3') | Reverse Primer (5'-3') | NCBI Accession Number |
|---|---|---|---|
| Beta actin | CTATGCTCTCCCTCACGCCATC (SEQ ID NO: 1) | CCACGCTCGGTCAGGATCTTC (SEQ ID NO: 2) | NM_007393.3 |
| Adiponectin | GCCGCTTATGTGTATCGCTCAG (SEQ ID NO: 3) | GCCAGTGCTGCCGTCATAATG (SEQ ID NO: 4) | NM_009605.4 |
| PPARγ2 | GGAAGCCCTTTGGTGACTTTATGG (SEQ ID NO: 5) | GCAGCAGGTTGTCTTGGATGTC (SEQ ID NO: 6) | NM_011146.3 |
| UCP2 | GCTGGTGGTGGTCGGAGATAC (SEQ ID NO: 7) | CATTACGGGCAACATTGGGAGAAG (SEQ ID NO: 8) | NM_011671.4 |
| FAS | GGTTCTAGCCAGCAGAGTCTACAG (SEQ ID NO: 9) | CTCGTTGTCACATCAGCCACTTG (SEQ ID NO: 10) | NM_007988.3 |

9. Statistical Analysis

A two-way analysis of variance (ANOVA), with repeated measures on one factor, (Statistica V7, Statsoft USA) was used to analyse body weight and food and water consumption between each group. All other data were analysed using one-way ANOVA. Sigmaplot (9.0, California, USA) was utilised to calculate the area under the curve of the glucose tolerance test. This was conducted using the trapezoidal rule and was followed by a one-way ANOVA to assess group differences. Post-hoc Fisher PLSD tests were conducted where appropriate. All results are presented as mean±SEM. A p-value of less than 0.05 was considered significant.

Results—Summary

Consumption by animals of the extract of the invention in the experimental diet-induced-obesity model resulted in a >20% reduction of body fat (visceral and peripheral) and a concomitant decrease in overall body weight of about 9% in a dose-dependent manner (statistically significant) over the 12 week study period. Decreased body weight gain and body fat was observed after treatment with a 4% extract of the invention. A consistent trend was observed after treatment with a 2% extract, but the results were not statistically significant for all parameters tested.

Detailed Results

Food and fluid intake: ANOVA analysis of the daily food and fluid intake patterns of the mice throughout the experimental period confirmed that there was no difference in food intake between the groups at any time during the experiment (data not shown). This confirms that the decreased body weight and body fat was not attributable to decreased food intake. The 4% extract group however did drink more than the control group (data not shown).

Fat levels: Dual Energy X-ray Absorptiometry (DEXA) was conducted at the end of the experimental period. The fat and fat-free mass of the mice was quantified and the results are illustrated in FIGS. 1A and B. ANOVA analyses revealed that the 4% group had less fat mass than the control group, $F(2, 38)=3.32$, $p=0.047$, however there were no differences between the groups for the measure of fat-free mass, $F(2, 38)=0.073$, $p=0.930$.

Figure 2A:
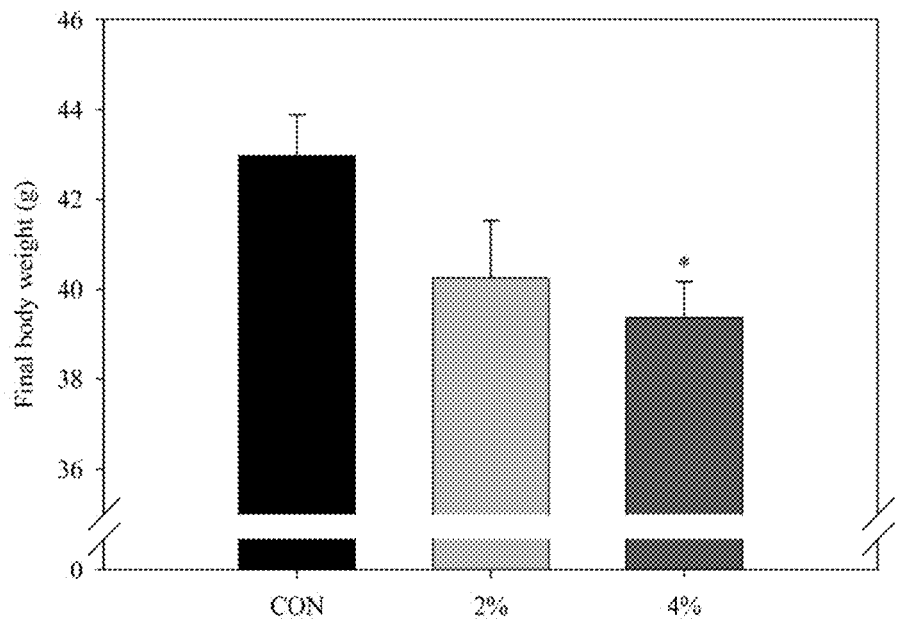
FIG. 2A: Mean (±SEM) final body weight for the three experimental groups. * p<0.05—denotes significant difference from the control group. (CON—control; 2%-2% extract; 4%-4% extract).
Figure 2B:
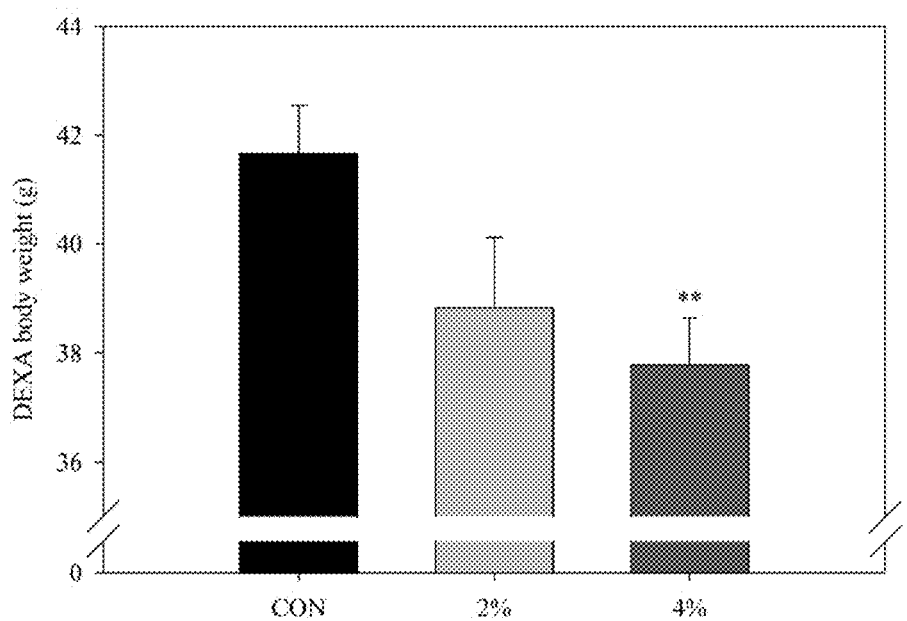
FIG. 2B: Mean (±SEM) DEXA body weight for the three experimental groups. ** p<0.01—denotes significant difference from the control group. (CON—control; 2%-2% extract; 4%-4% extract).

Final body weight (determined by measuring the animals post-mortem) and body weight measured by DEXA (which does not measure fluids) are illustrated in FIGS. 2A and B. They both demonstrate that the 4% group had lower body weight relative to control at the conclusion of the experiment ($F(2, 38)=3.54$, $p=0.040$; $F(2, 38)=3.94$, $p=0.030$).

Adverse effects: Bone mineral density and bone mineral content were also measured using DEXA. The results of these analyses indicated that there was no difference between the groups for either of these measures (data not shown), indicating that the extracts had no deleterious effects on bone growth or development over the 12 week study. The complete absence of any acute or chronic toxicity or observable adverse physiological or metabolic effects throughout the study period suggests that relatively high doses of the extract of the invention are well tolerated in this pre-clinical animal model.

Figure 3:
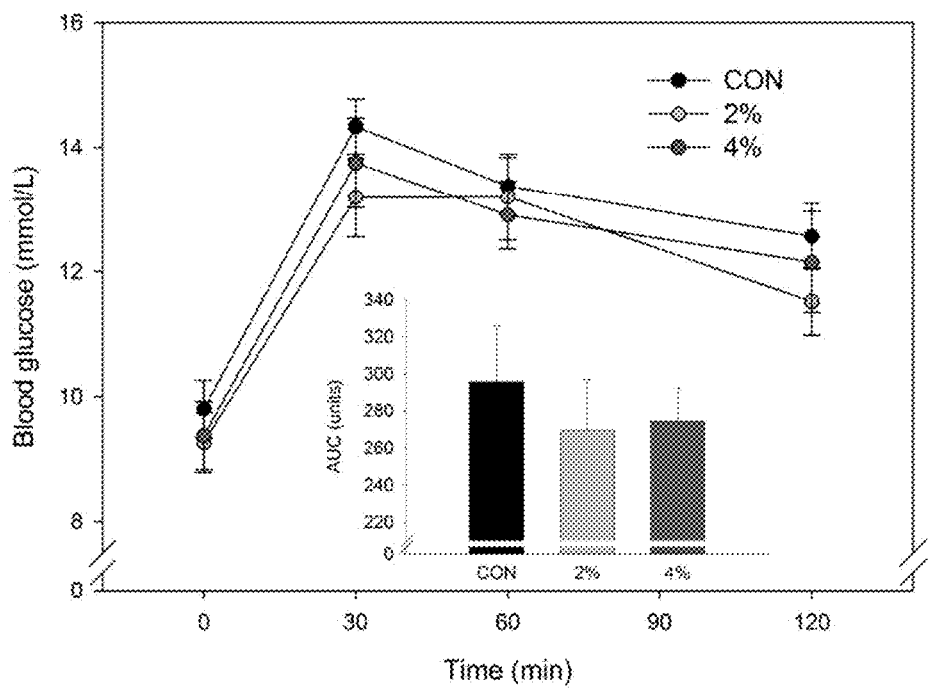
FIG. 3: Glucose tolerance curve showing changes in blood glucose concentration (mmol/L) prior to and following administration of glucose solution. (CON—control; 2%-2% extract; 4%-4% extract; AUC—area under the curve).

Glucose tolerance: Blood glucose levels were examined in the mice prior to and at 30-minute intervals following a glucose load. The results of the glucose tolerance test are shown in FIG. 3, and demonstrate that there were no differences between the three groups in their clearance of glucose, $F(2, 39)=0.59$, $p=0.558$. The similarity in glucose-tolerance profiles of between the animals consuming extracts of the invention and those consuming a control diet confirms adequate pancreatic function in both animal populations (i.e. no evidence of insulin-tolerance developing).

Figure 4A:
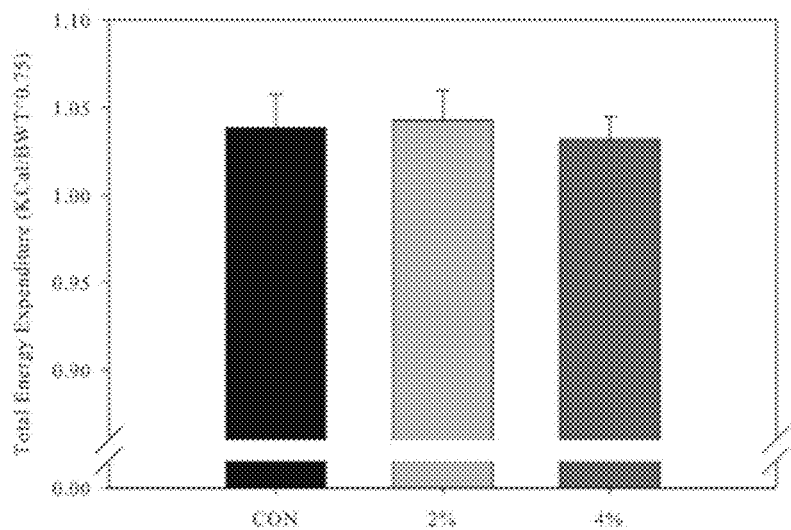
FIG. 4A: Mean (±SEM) 24-hour energy expenditure of mice on the experimental diets (CON—control; 2%-2% extract; 4%-4% extract).
Figure 4B:
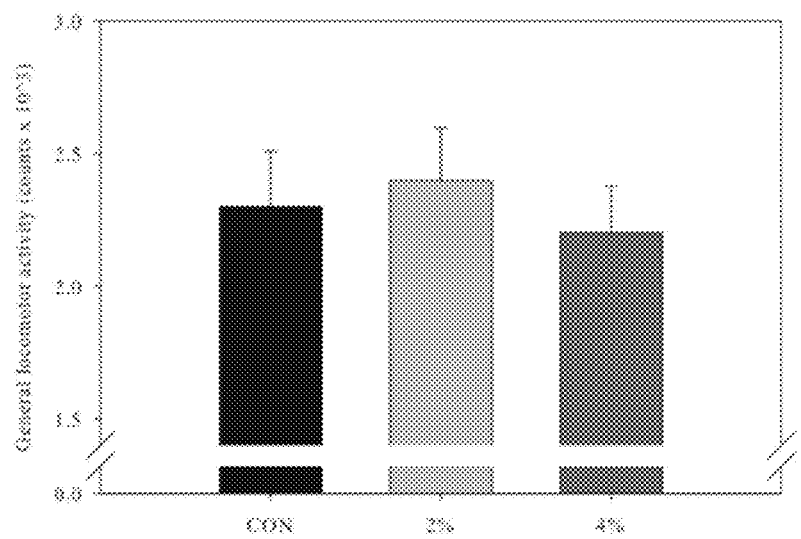
FIG. 4B: Mean (±SEM) general locomotor activity of mice on the experimental diets over a 24-hour period (CON—control; 2%-2% extract; 4%-4% extract).

Energy expenditure: In the first week of animals receiving the experimental diets metabolic rate was measured via indirect calorimetry in the Labmaster system. At this time general locomotor activity was also measured. No differences were observed in either of these measures. No changes were observed in energy expenditure as evaluated by these methods, indicating that an increase in metabolism with extracts of the invention may not be the mechanism of reduced weight gain (FIGS. 4A and B).

Figure 5A:
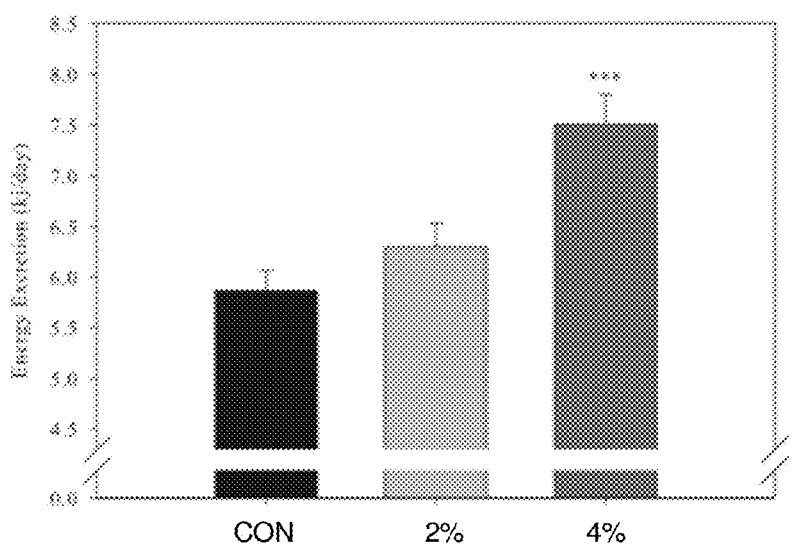
FIG. 5A: Mean (±SEM) Daily-excreted energy of mice on the experimental diets *** p<0.001—denotes significant difference from the control group. (CON—control; 2%-2% extract; 4%-4% extract).
Figure 5B:
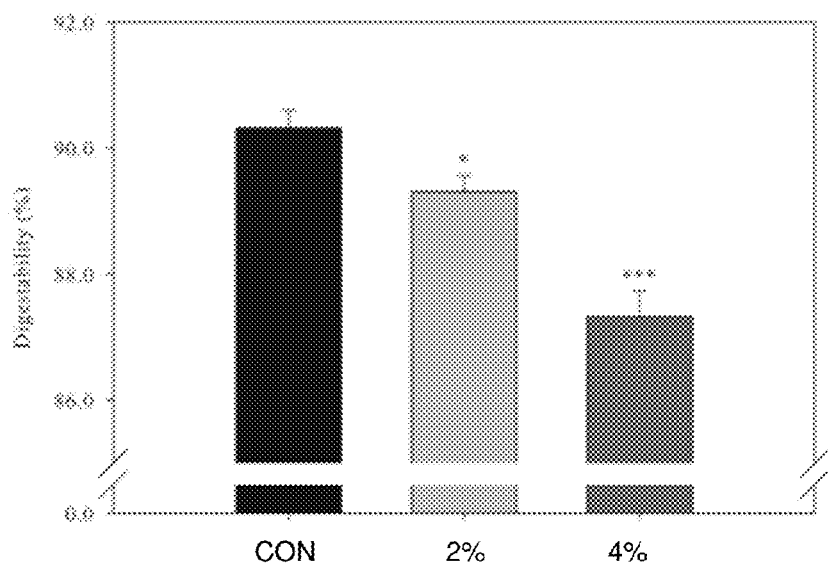
FIG. 5B: Mean (±SEM) Digestibility, the percentage of energy that was digested from the diet consumed, for mice in each of the experimental groups. * p<0.05 *** p<0.001—denotes significant difference from the control group. (CON—control; 2%-2% extract; 4%-4% extract).

Faecal energy excretion: Excreted energy was assessed in the faecal output of the mice after 8 weeks on the experimental diets. The total energy output was greater in 4% extract treated mice compared to control (FIG. 5A). Digestibility of the energy within the diets was reduced in both groups receiving extracts of the invention (FIG. 5B). Increased faecal energy excretion supports the hypothesis that that reduced energy absorption is the mechanism responsible for reduced weight gain in the animals consuming extracts of the invention.

Figure 5C:
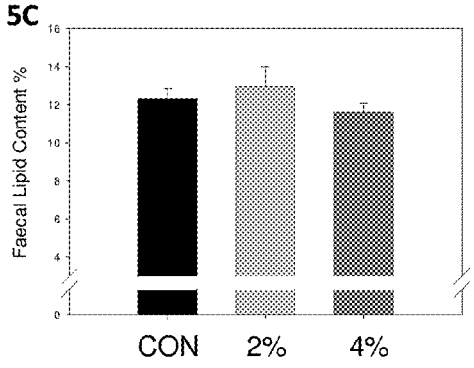
FIGS. 5C, 5D, and 5E: Percentage differences (±SEM) of faecal matter analyses for (C) lipid, (D) carbon and (E) nitrogen levels. *P<0.05, ***P<0.001 denotes significance difference from control group. (CON—control; 2%-2% extract; 4%-4% extract).
Figure 5D:
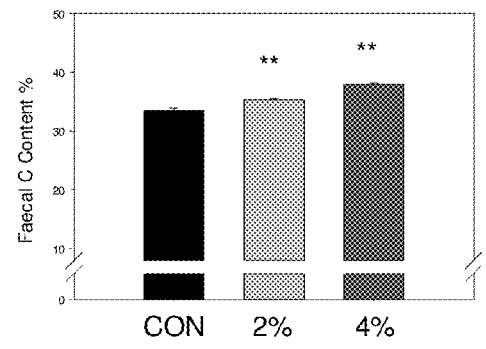
Figure 5E:
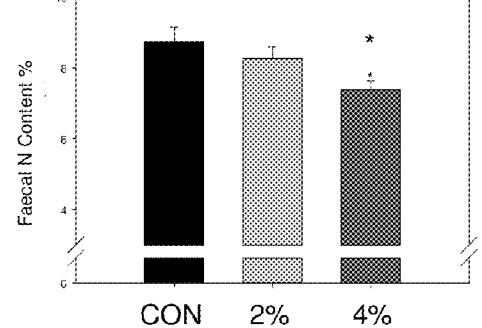
Figure 5F:
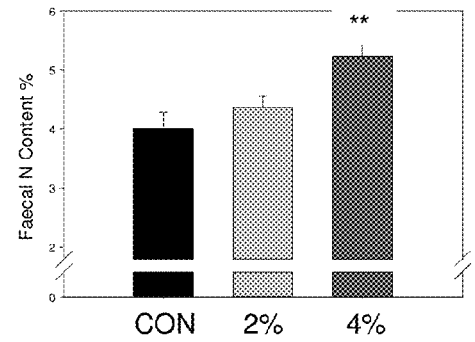
FIG. 5F: Ratio of carbon to nitrogen in the faecal matter. *P<0.05, ***P<0.001 denotes significance difference from control group. (CON—control; 2%-2% extract; 4%-4% extract).

Faecal Lipid, Carbon (C) and Nitrogen (N) content: The cause for the increase in faecal energy mentioned above was examined There was no significant difference in the faecal lipid contents between the experimental groups and the control group (FIG. 5C). One-way ANOVA analyses revealed that the faecal C content, indicative of carbohydrate level, in both PME treatment groups was higher relative to the control group (FIG. 5D). The faecal N content, indicative of protein content, was lower in mice whose diet was supplemented with 4% PME when compared to that of the control (FIG. 5E). The C/N ratio was significantly different between the control mice and those whose diet was supplemented with 4% PME (FIG. 5F).

Figure 6A:
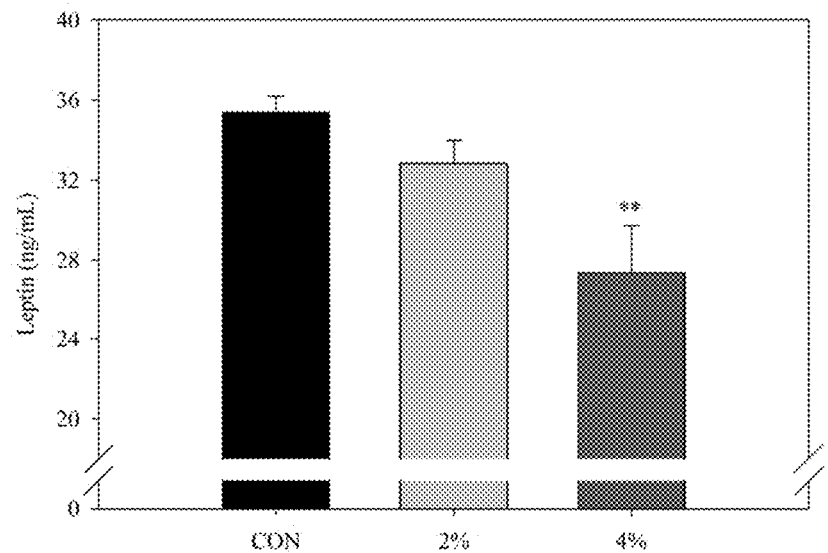
FIG. 6A: Mean (±SEM) plasma leptin levels for mice in each of the experimental groups. ** p<0.01—denotes significant difference from the control group. (CON—control; 2%-2% extract; 4%-4% extract).
Figure 6B:
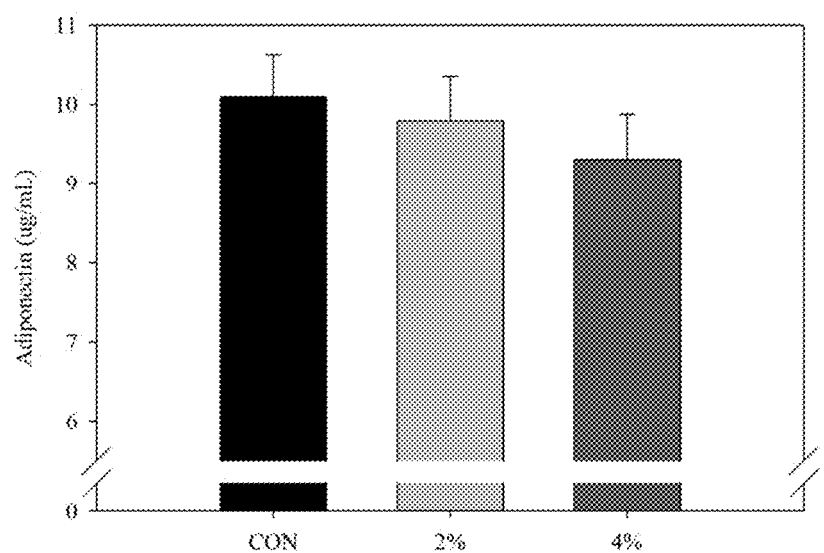
FIG. 6B: Mean (±SEM) plasma adiponectin levels for mice in each of the experimental groups. (CON—control; 2%-2% extract; 4%-4% extract).

Adipokines: The ELISA assay of plasma leptin identified significantly lower leptin levels in mice in the 4% group relative to the control group (FIG. 6). Leptin is a 16 kDa protein hormone that plays a key role in regulating energy intake and energy expenditure, including appetite and metabolism. Leptin acts on receptors in the hypothalamus of the brain where it inhibits appetite by counteracting the effects of feeding stimulants such as neuropeptide Y and anandamide, as well as promoting the synthesis of α-MSH, an appetite suppressant. The absence of leptin (or its receptor) is thought to lead to uncontrolled food intake. The fact that mice in the 4% group having decreased body fat also had lower levels of leptin substantiates the data relating to decreased body fat accumulation.

There were only minor differences in circulating plasma adiponectin levels between any of the groups, suggesting that the reduced fat deposition in animals receiving extracts of the invention was not due to increased energy expenditure, but more likely reduced caloric adsorption (ie reduced energy absorption).

Figure 7A:
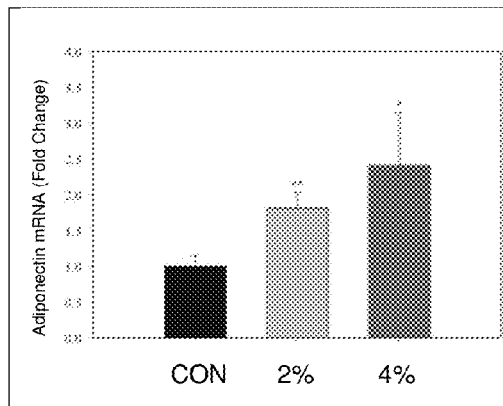
FIG. 7A: Mean (±SEM) fold change adipose adiponectin mRNA expression for mice in each of the experimental groups. * p<0.05 ** p<0.01—denotes significant difference from the control group. (CON—control; 2%-2% extract; 4%-4% extract).
Figure 7B:
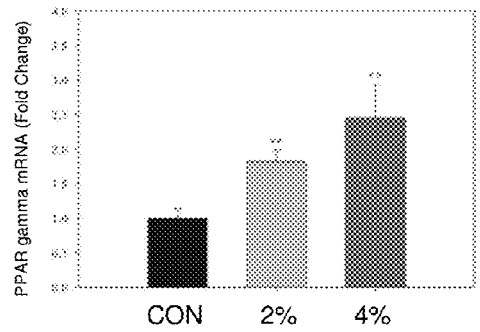
FIG. 7B: Mean (±SEM) fold change adipose PPARy mRNA expression for mice in each of the experimental groups. ** p<0.01—denotes significant difference from the control group. (CON—control; 2%-2% extract; 4%-4% extract).
Figure 7C:
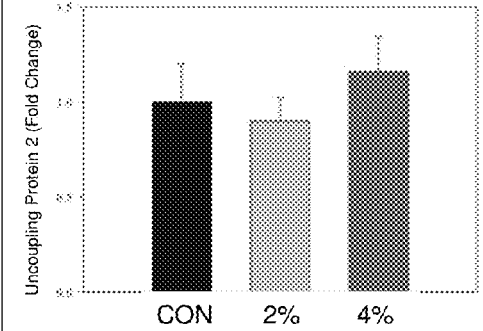
FIG. 7C: Mean (±SEM) fold change adipose UCP2 mRNA expression for mice in each of the experimental groups. (CON—control; 2%-2% extract; 4%-4% extract).
Figure 7D:
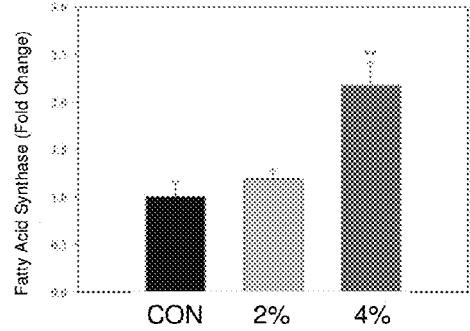
FIG. 7D: Mean (±SEM) fold change adipose FAS mRNA expression for mice in each of the experimental groups. ** p<0.01—denotes significant difference from the control group. (CON—control; 2%-2% extract; 4%-4% extract).

Gene expression—adipose tissue: Gene expression was analysed in the adipose tissue of animals from the experimental groups. Administration of both 2% and 4% of the extract of the invention resulted in increased expression of adiponectin (released primarily by small adipocytes, involved in glucose regulation and fatty acid catabolism) and peroxisome proliferator-activated receptor (PPAR) gamma (involved in fatty acid storage and glucose metabolism) genes relative to control animals (FIGS. 7A and B). There were no differences in uncoupling protein 2 (UCP2) (involved in energy expenditure) (FIG. 7C). Administration of the extract of the invention at 4% also increased fatty acid synthase (FAS) expression, involved in the synthesis of fatty acids (FIG. 7D). Increases in gene expression of adiponectin, PPAR-gamma and FAS are consistent with a reduction in body adiposity, possibly due to reduced energy absorption. Increased expression of PPAR-gamma and FAS is consistent with improved insulin sensitivity.

Figure 8A:
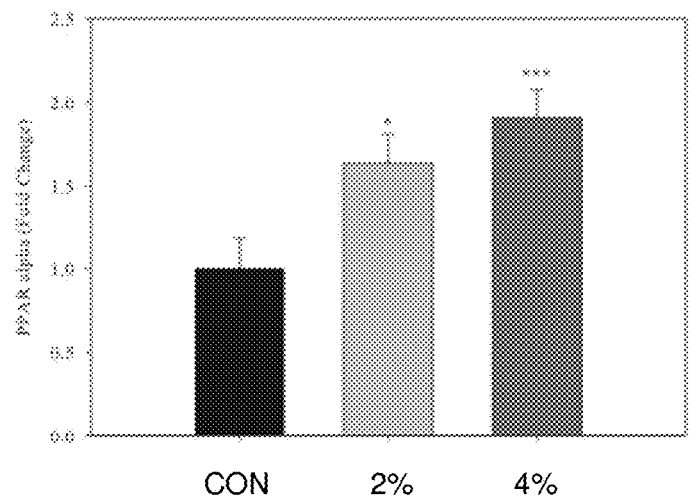
FIG. 8A. Mean (±SEM) fold change liver PPARc mRNA expression for mice in each of the experimental groups. * p<0.05 *** p<0.001—denotes significant difference from the control group. (CON—control; 2%-2% extract; 4%-4% extract).
Figure 8B:
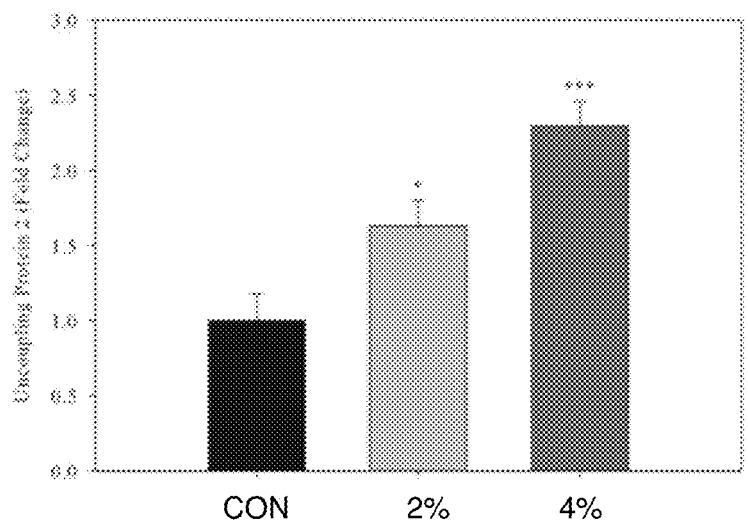
FIG. 8B. Mean (±SEM) fold change liver UCP2 mRNA expression for mice in each of the experimental groups. * p<0.05 *** p<0.001—denotes significant difference from the control group. (CON—control; 2%-2% extract; 4%-4% extract).

Liver mRNA expression: Gene expression was also analysed in the liver. Administration of both 2% and 4% of the extract of the invention treatment resulted in increased expression of PPAR alpha relative to control animals (FIG. 8A) and UCP2 (FIG. 8B).

Figure 9:
FIG. 9: MRI analysis of the fat distribution in mice from the control, 2% extract and 4% extract group.
Figure 10:
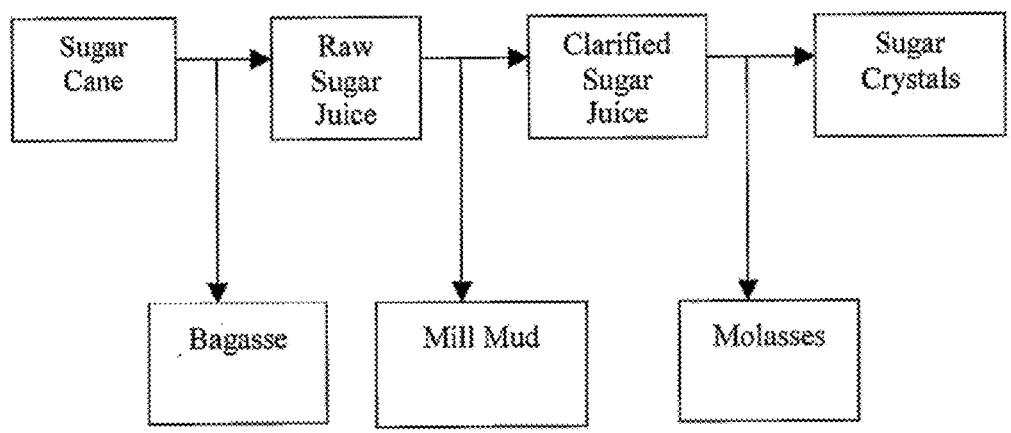
FIG. 10: Shows the processing steps required to produce white sugar.
Figure 11:
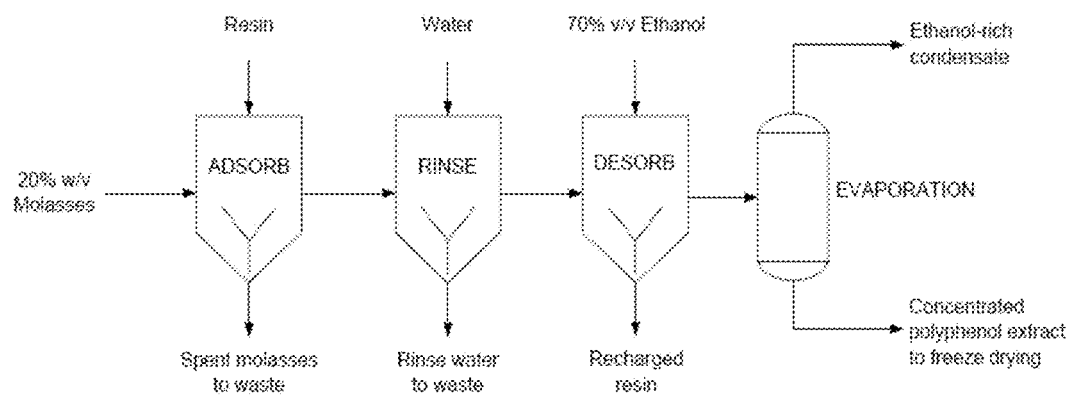
FIG. 11: Shows a method involving the step of passing molasses over a hydrophobic polymeric adsorbent to produce the extract of the invention having a higher relative abundance of hydrophobic compounds including polyphenols compared to molasses that has not been exposed to a polymeric adsorbent.

MRI analysis of the fat distribution: After 14 weeks (2 weeks after the cessation of dietary supplementation), the body fat deposition of 6 mice (n=2 per group) was assessed with magnetic resonance imaging (MRI). Consumption by animals of the extract of the invention in the experimental diet-induced-obesity model resulted in a decrease in total body fat (visceral and peripheral). FIG. 9 illustrates a typical result seen between control mice and those receiving 2% and 4% of the extract of the invention.

Modifications and improvements to the invention will be readily apparent to those skilled in the art. Such modifications and improvements are intended to be within the scope of this invention. The foregoing description details certain embodiments of the invention. It will be appreciated, however, that no matter how detailed the foregoing appears in text, the invention can be practiced in many ways. As is also stated above, it should be noted that the use of particular terminology when describing certain features or aspects of the invention should not be taken to imply that the terminology is being re-defined herein to be restricted to including any specific characteristics of the features or aspects of the invention with which that terminology is associated. The scope of the invention should therefore be construed in accordance with the appended claims and any equivalents thereof.

The invention claimed is:

1. A method for producing a molasses extract comprising the steps of:

a. diluting the molasses to produce a 10 to 40% w/v aqueous solution;

b. optionally filtering the diluted molasses produced in step (a);

c. contacting the diluted molasses with a hydrophobic polymeric adsorbent under conditions sufficient to enable binding of hydrophobic compounds to the adsorbent and flow through of all other compounds in the diluted molasses;

d. optionally passing the flow through from step (c) over the hydrophobic polymeric adsorbent at least once;

e. optionally rinsing the hydrophobic polymeric adsorbent; and f. eluting the compounds bound to the hydrophobic polymeric adsorbent to produce the extract;

wherein the hydrophobic compounds are eluted with 30 to 70% ethanol; and wherein the molasses extract has a high relative abundance of hydrophobic compounds including polyphenols and wherein the extract comprises:
at least 9000 mg catechin equivalent/100 g of hydrophobic polyphenols in a mixture of free form polyphenols selected from the group consisting of apigenin, catechin, catechin gallate, epicatechin, kaempherol, luteolin, quercetin, tricin, myricetin and diosmetin; polyphenol glycosides selected from diosmin, tricin-7-O-neohesperidoside, orientin, vitexin, luteolin-8-C-(rhamnosylglucoside), schaftoside, isoschaftoside and rutin; and phenolic acids, selected from caffeic acid, chlorogenic acid, p-coumaric acid, ferulic acid, gallic acid, syringic acid and vanillic acid;
one or more trace elements selected from the group consisting of calcium, iron, magnesium, manganese, potassium and sodium;
protein and other nitrogen-containing compounds;
carbohydrates other than monosaccharides and sucrose; and
less than 2 g of monosaccharides and sucrose per 100 g of extract.

2. The method according to claim 1, wherein the method does not include a centrifugation step.

3. The method according to claim 1, wherein the filtration step of (b) does not include ultrafiltration.

4. The method according to claim 1, wherein the filtration step of (b) includes filtering the diluted molasses produced in step (a) through a microfiltration membrane.

5. The method according to claim 4, wherein the microfiltration includes a membrane with a pore size of between 0.1 to 0.5 micron.

6. The method according to claim 5, wherein the membrane has a pore size of 0.1 micron.

7. The method according to any one of claim 1, wherein the hydrophobic compounds are eluted with 70% ethanol.

8. The method according to any one of claim 1, wherein the molasses extract comprises at least one of diosmin, chlorogenic acid, and syringic acid.

9. The method according to any one of claim 1, wherein the molasses extract comprises at least 18000 mg catechin equivalent/100 g of hydrophobic polyphenols.

10. The method according to claim 9, wherein the molasses extract comprises at least 21000 mg catechin equivalent/100 g of hydrophobic polyphenols.

11. The method according to any one of claim 1, wherein the molasses extract has less than 1 g of monosaccharides and sucrose per 100 g of extract.

12. The method according to any one of claim 1, wherein the hydrophobic polymeric adsorbent is a polystyrene adsorbent.

13. The method according to any one of claim 1, wherein the hydrophobic polymeric adsorbent is a food grade adsorbent.

14. The method according to any one of claim 1, wherein the hydrophobic polymeric adsorbent is Amberlite XAD16 or FPX66.

15. The method according to any one of claim 1, wherein the method includes the filtration step (b) and no other pre-treatment steps prior to step (c).

16. A method according to any one of claim 1, wherein step (c) comprises loading the diluted molasses on to the hydrophobic polymeric adsorbent at a flow rate of 2 to 6 L/min.

17. A method according to claim 16, wherein the flow rate is 4 L/min.

18. A method according to any one of claim 1, wherein in step (c) the diluted molasses is in contact with the hydrophobic polymeric adsorbent for a period of 30-120 minutes.

19. A method according to claim 18, wherein in step (c) the diluted molasses is in contact with the hydrophobic polymeric adsorbent for at least 60 minutes, at ambient temperature.

20. A method according to any one of claim 1, wherein in step (d) the flow through from step (c) is passed over the hydrophobic polymeric adsorbent once or twice.

* * * * *